United States Patent
Zhang et al.

(10) Patent No.: US 10,460,440 B2
(45) Date of Patent: Oct. 29, 2019

(54) DEEP CONVOLUTIONAL NEURAL NETWORK WITH SELF-TRANSFER LEARNING

(71) Applicant: General Electric Company, Schenectady, NY (US)

(72) Inventors: Min Zhang, San Ramon, CA (US); Gopal Biligeri Avinash, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 56 days.

(21) Appl. No.: 15/792,698

(22) Filed: Oct. 24, 2017

(65) Prior Publication Data

US 2019/0122360 A1 Apr. 25, 2019

(51) Int. Cl.
*G06K 9/00* (2006.01)
*G06T 7/00* (2017.01)
(Continued)

(52) U.S. Cl.
CPC .......... *G06T 7/0012* (2013.01); *G06K 9/6267* (2013.01); *G06K 9/6273* (2013.01);
(Continued)

(58) Field of Classification Search
CPC ........ G06N 3/084; G06N 3/0454; G06N 3/08; G06N 3/04; G06N 3/082; G06N 3/02;
(Continued)

(56) References Cited

U.S. PATENT DOCUMENTS 5,769,074 A 6/1998 Barnhill et al.
9,607,373 B2 3/2017 Buisseret et al.
(Continued)

FOREIGN PATENT DOCUMENTS

CN 106952338 A 7/2017
CN 107067396 A 8/2017
(Continued)

OTHER PUBLICATIONS

Dubost, F., et al., "GP-Unet: Lesion Detection from Weak Labels with a 3D Regression Network," International Conference on Medical Image Computing and Computer-Assisted Intervention, MICCAI, pp. 214-221 (Sep. 4, 2017).
(Continued)

*Primary Examiner* — Jose L Couso
(74) *Attorney, Agent, or Firm* — Amin, Turocy & Watson, LLP

(57) ABSTRACT

Systems and techniques for facilitating a deep convolutional neural network with self-transfer learning are presented. In one example, a system includes a machine learning component, a medical imaging diagnosis component and a visualization component. The machine learning component generates learned medical imaging output regarding an anatomical region based on a convolutional neural network that receives medical imaging data. The machine learning component also performs a plurality of sequential down-sampling and upsampling of the medical imaging data associated with convolutional layers of the convolutional neural network. The medical imaging diagnosis component determines a classification and an associated localization for a portion of the anatomical region based on the learned medical imaging output associated with the convolutional neural network. The visualization component generates a multi-dimensional visualization associated with the classification and the localization for the portion of the anatomical region.

20 Claims, 15 Drawing Sheets

(51) Int. Cl.
*G06K 9/62* (2006.01)
*G16H 50/20* (2018.01)
*G06N 3/04* (2006.01)

(52) U.S. Cl.
CPC .......... *G06N 3/0454* (2013.01); *G16H 50/20* (2018.01); *G06T 2207/10081* (2013.01); *G06T 2207/10116* (2013.01); *G06T 2207/20081* (2013.01); *G06T 2207/20084* (2013.01); *G06T 2207/30004* (2013.01); *G06T 2207/30008* (2013.01); *G06T 2207/30048* (2013.01); *G06T 2207/30061* (2013.01); *G06T 2207/30096* (2013.01)

(58) Field of Classification Search
CPC ........ G06N 3/067; G06N 5/003; G06N 20/00; G06N 20/20; G06T 7/0012; G06T 7/337; G06T 7/001; G06T 7/11; G06T 7/33; G06T 2207/30168; G06T 2207/20084; G06T 2207/10004; G06T 2207/20021; G06T 2207/10016; G06T 2207/20008; G06T 2207/20076; G06T 2207/30004; G06T 2207/10081; G06T 2207/10088; G06T 2207/10104; G06T 2207/10108; G06T 2207/10116; G06T 2207/10132; G06T 2210/41; G06K 9/6232; G06K 9/036; G06K 9/4642; G06K 9/4628; G06K 9/66; G06K 9/6269; G06K 9/6277; G06K 9/46; G06K 9/6215; G06K 9/6255; G06K 9/627; G06K 9/629; G06K 9/6292; G06K 9/0061; G06K 9/623; G06K 9/6256; G06K 9/6274; G06K 9/6284; G06K 9/00684; G06K 9/4604; G06K 9/6265; G06K 9/6267; G06K 9/00127; G06K 9/00496; G06K 9/6289; G06K 2209/05; H04N 21/4666; H04N 2201/0079; G06F 17/27; G06F 19/00; G06F 19/30; G06F 19/32; G06F 19/34; G06F 19/3418; G06F 19/70; G16H 50/00; G16H 50/20; G16H 50/30; G16H 50/50; G16H 50/70; G16H 50/80
See application file for complete search history.

(56) References Cited

U.S. PATENT DOCUMENTS

| | | | |
|---|---|---|---|
| 10,140,544 B1* | 11/2018 | Zhao ............... | G06N 3/084 |
| 10,192,640 B2* | 1/2019 | Itu .................. | G16H 30/20 |
| 2003/0194124 A1* | 10/2003 | Suzuki ............. | G06T 7/0012 382/156 |
| 2009/0082637 A1 | 3/2009 | Galperin | |
| 2012/0051608 A1 | 3/2012 | Avinash et al. | |
| 2012/0070044 A1 | 3/2012 | Avinash et al. | |
| 2016/0300120 A1 | 10/2016 | Haas et al. | |
| 2017/0024641 A1 | 1/2017 | Wierzynski | |
| 2017/0039708 A1 | 2/2017 | Henry et al. | |
| 2017/0185871 A1* | 6/2017 | Zhang ............... | G06N 3/0454 |
| 2017/0200260 A1 | 7/2017 | Bhaskar et al. | |
| 2017/0213339 A1 | 7/2017 | Hibbard et al. | |
| 2017/0270653 A1* | 9/2017 | Garnavi ............ | G06T 7/0002 |
| 2017/0287134 A1* | 10/2017 | Abedini ............ | G06K 9/622 |
| 2018/0247195 A1* | 8/2018 | Kumar .............. | G06N 3/08 |
| 2018/0253531 A1* | 9/2018 | Sharma ............. | G16H 30/20 |
| 2018/0263585 A1* | 9/2018 | Weiss ............... | A61B 5/4824 |
| 2018/0315193 A1* | 11/2018 | Paschalakis ....... | G06T 7/0016 |
| 2018/0350066 A1* | 12/2018 | Zuyev .............. | G06T 7/0012 |
| 2018/0360313 A1* | 12/2018 | Zhang .............. | A61B 5/004 |
| 2019/0005684 A1* | 1/2019 | De Fauw ........... | G06K 9/6262 |

FOREIGN PATENT DOCUMENTS

| | | |
|---|---|---|
| CN | 107256396 A | 10/2017 |
| WO | 2010/005969 A2 | 1/2010 |

OTHER PUBLICATIONS

Hwang, S., and Kim, H-E., "Self-Transfer Learning for Fully Weakly Supervised Object Localization," arxiv.org, Cornell University Library, 201OLIN Library Cornell University Ithaca, NY 14853, pp. 1-9 (Feb. 4, 2016).

Oktay, O., et al., "Anatomically Constrained Neural Networks (ACNN): Application to Cardiac Image Enhancement and Segmentation," IEEE Transactions on Medical Imaging, vol. 37, Issue 2, pp. 384-395 (Aug. 29, 2017).

Payer, C., et al., "Multi-Label Whole Heart Segmentation Using CNNs and Anatomical Label Configurations," Institut for Computer Graphics and Vision, vol. 10663, pp. 190-198 (2017), Sep. 14, 2017 (Sep. 14, 2017).

Rohe, M-M., et al., "Automatic Multi-Atlas Segmentation of Myocardium with SVF-Net," Statistical Atlases and Computational Models of the Heart (STACOM), pp. 1-9 (Aug. 18, 2017).

Wang, X., et al., "ChestX-ray8: Hospital-Scale Chest X-Ray Database and Benchmarks on Weakly-Supervised Classification and Localization of Common Thorax Diseases," IEEE Conference on Computer Vision and Pattern Recognition (CVPR), pp. 3462-3471 (Jul. 21, 2017).

International Search Report and Written Opinion issued in connection with corresponding PCT Application No. PCT/US2018/018902 dated Jul. 2, 2018.

Hwang et al., "Self-Transfer Learning for Fully Weakly Supervised Object Localization," arXiv:1602.01625v1 [cs.CV], Feb. 4, 2016, 9 pages.

International Search Report and Written Opinion received for PCT Application Serial No. PCT/US2018/031779 dated Jul. 16, 2018, 9 pages.

Shin et al., "Deep Convolutional Neural Networks for Computer-Aided Detection: CNN Architectures, Dataset Characteristics and Transfer Learning", IEEE Transactions on Medical Imaging, vol. 35, No. 5, 2016, pp. 1-14.

Zhang et al., "Deep Learning Architecture for Automated Image Feature Extraction", U.S. Appl. No. 62/574,333, filed Oct. 19, 2017, 50 pages.

Zhang et al., "Image Analysis Using Deviation From Normal Data", U.S. Appl. No. 15/855,033, filed Dec. 27, 2017, 71 pages.

Zhang et al., "Training an Auto-Encoder on a Single Class", U.S. Appl. No. 15/854,980, filed Dec. 27, 2017, 69 pages.

Aljabar et al., "Multi-atlas based segmentation of brain images: Atlas selection and its effect on accuracy", NeuroImage, vol. 46, No. 3, Jul. 1, 2009, pp. 726-738.

Curiale et al., "Automatic Myocardial Segmentation by Using a Deep Deaming Network in Cardiac MRI", IEEE XLIII Latin American Computer Conference (CLEI), 2017, 6 pages.

International Search Report and Written Opinion received for PCT Application Serial No. PCT/US2018/017407 dated Jul. 4, 2018, 12 pages.

Zhang et al., "Building a Binary Neural Network Architecture", U.S. Appl. No. 15/855,015, filed Dec. 27, 2017, 76 pages.

International Search Report and Written Opinion received for PCT Application Serial No. PCT/US2018/031754 dated Aug. 16, 2018, 10 pages.

Dimitrievski et al., "High resolution depth reconstruction from monocular images and sparse point clouds using deep convolutional neural network", Proceedings of SPIE, vol. 10410, 2017, pp. 1-3.

Hosseini et al., "Derivative Kernels: Numerics and Applications", IEEE Transactions on Image Processing, vol. 26, No. 10, 2017, pp. 1-16.

Non-Final Office Action received for U.S. Appl. No. 15/855,033 dated Aug. 21, 2019, 36 pages.

* cited by examiner

DEEP CONVOLUTIONAL NEURAL NETWORK WITH SELF-TRANSFER LEARNING

TECHNICAL FIELD

This disclosure relates generally to artificial intelligence.

BACKGROUND

Artificial Intelligence (AI) can be employed for classification and/or analysis of digital images. For instance, AI can be employed for image recognition. In certain technical applications, AI can be employed to enhance medical imaging diagnosis. Diseases of a patient can be classified, for example, by analyzing medical images of the patient using a deep neural network. In an example, region-of-interest based deep neural networks can be employed to localize a disease in an anatomical region of a patient. However, accuracy and/or efficiency of a classification and/or an analysis of digital images using conventional artificial techniques is generally difficult to achieve. Furthermore, conventional artificial techniques for classification and/or analysis of digital images generally requires labor-intensive processes such as, for example, pixel annotations, voxel level annotations, etc. As such, conventional artificial techniques for classification and/or analysis of digital images can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes a machine learning component, a medical imaging diagnosis component and a visualization component. The machine learning component generates learned medical imaging output regarding an anatomical region based on a convolutional neural network that receives medical imaging data. The machine learning component also performs a plurality of sequential downsampling and upsampling of the medical imaging data associated with convolutional layers of the convolutional neural network. The medical imaging diagnosis component determines a classification and an associated localization for a portion of the anatomical region based on the learned medical imaging output associated with the convolutional neural network. The visualization component generates a multi-dimensional visualization associated with the classification and the localization for the portion of the anatomical region.

According to another embodiment, a method is provided. The method provides for receiving, by a system comprising a processor, medical imaging data for a patient body. The method also provides for performing, by the system, iterative sequential downsampling and upsampling of the medical imaging data associated with convolutional layers of a convolutional neural network to generate learned medical imaging output regarding the patient body. Furthermore, the method provides for classifying, by the system, a disease for a portion of the patient body based on the learned medical imaging output associated with the convolutional neural network. The method also provides for generating, by the system, a multi-dimensional visualization associated with the classifying of the disease for the portion of the patient body.

According to yet another embodiment, a method is provided. The method provides for receiving, by a system comprising a processor, medical imaging data that comprises a set of medical images. The method also provides for training, by the system, a convolutional neural network by performing iterative sequential downsampling and upsampling of the medical imaging data associated with convolutional layers of the convolutional neural network. Furthermore, the method provides for generating, by the system, a set of filter values for the convolutional neural network based on the iterative sequential downsampling and upsampling of the medical imaging data.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
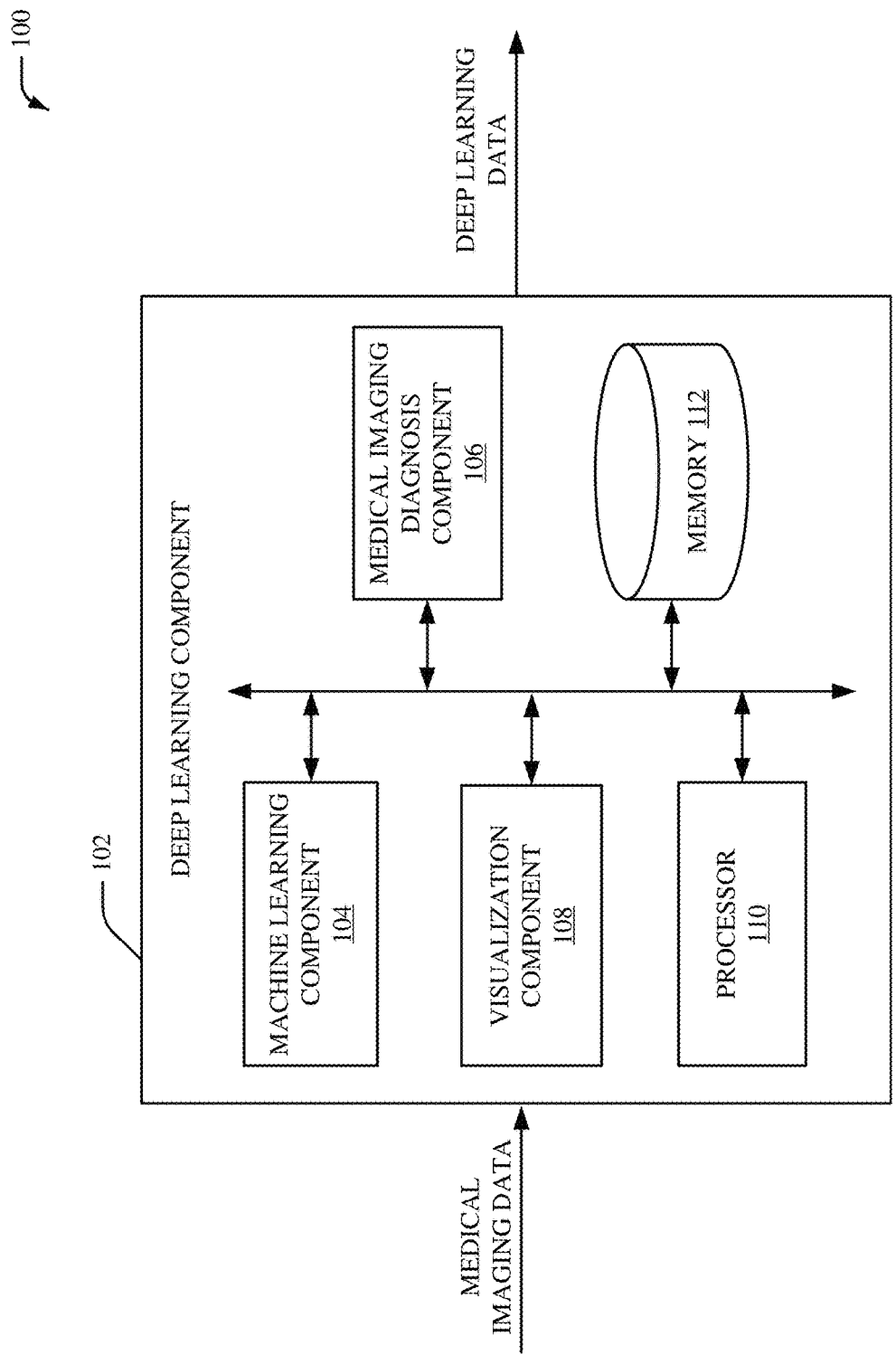
FIGS. 1-6 illustrate a high-level block diagram of an example deep learning component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for performing self-transfer learning associated with a deep convolutional network are presented. For example, as compared to conventional artificial intelligence (AI) techniques, the subject innovations provide for a novel weakly supervised AI framework with self-transfer learning. The novel weakly supervised AI framework can perform machine learning (e.g., deep learning) associated with a deep convolutional network by employing image-level labels to classify and/or localize a disease over a particular anatomical region associated with medical imaging data. In an aspect, the novel weakly supervised AI framework can comprise shared convolutional layers containing sequential down sampling and/or sequential up sampling. Additionally or alternatively, the novel weakly supervised AI framework can comprise fully connected layers and/or class activation maps. As such, by employing the novel weakly supervised AI framework to analyze medical imaging data, detection and/or localization of diseases for a patient associated with the medical imaging data can be improved. Furthermore, accuracy and/or efficiency for classification and/or analysis of digital images (e.g., medical imaging data) can be improved. Moreover, effectiveness of a machine learning model for classification and/or analysis of digital images (e.g., medical imaging data) can be improved, performance of one or more processors that execute a machine learning model for classification and/or analysis of digital images (e.g., medical imaging data) can be improved, and/or efficiency of one or more processors that execute a machine learning model for classification and/or analysis of digital images (e.g., medical imaging data) can be improved.

Referring initially to FIG. 1, there is illustrated an example system 100 that provides a deep convolutional neural network with self-transfer learning, according to an aspect of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In one example, the system 100 can be associated with a viewer system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include a deep learning component 102 that can include a machine learning component 104, a medical imaging diagnosis component 106 and a visualization component 108. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the deep learning component 102) can include memory 112 for storing computer executable components and instructions. The system 100 (e.g., the deep learning component 102) can further include a processor 110 to facilitate operation of the instructions (e.g., computer executable components and instructions) by the system 100 (e.g., the deep learning component 102).

The deep learning component 102 (e.g., the machine learning component 104) can receive medical imaging data (e.g., MEDICAL IMAGING DATA shown in FIG. 1). The medical imaging data can be two-dimensional medical imaging data and/or three-dimensional medical imaging data generated by one or more medical imaging devices. For instance, the medical imaging data can be electromagnetic radiation imagery captured via a set of sensors (e.g., a set of sensors associated with a medical imaging device). In certain embodiments, the medical imaging data can be a series of electromagnetic radiation imagery captured via a set of sensors (e.g., a set of sensors associated with a medical imaging device) during an interval of time. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, an x-ray device, a computed tomography (CT) device, another type of medical imaging device, etc. The machine learning component 104 can perform a machine learning process (e.g., an artificial intelligence process for machine learning) based on the medical imaging data. In an aspect, the machine learning component 104 can perform deep learning to facilitate classification and/or localization of one or more diseases associated with the medical imaging data. In another aspect, the machine learning component 104 can perform deep learning based on a convolutional neural network that receives the medical imaging data.

In an embodiment, the machine learning component 104 can perform a training phase for the machine learning process. For example, the medical imaging data can be a set of medical images (e.g., a set of x-ray images, etc.) stored in a data store. Furthermore, the machine learning component 104 can perform the training phase for the machine learning process based on the set of medical images stored in a data store to train a neural network model (e.g., a neural network model for the convolutional neural network). In certain embodiments, the machine learning component 104 can employ a first portion of the medical imaging data for training associated with the convolutional neural network, a second portion of the medical imaging data for validation associated with the convolutional neural network, and a third portion of the medical imaging data for testing associated with the convolutional neural network. Additionally or alternatively, the machine learning component 104 can randomly select a set of medical images from a training set associated with the medical imaging data for data augmentation associated with the medical imaging data. In an aspect, the machine learning component 104 can modify an orientation of the set of medical images for the data augmentation associated with the medical imaging data. In one example, the machine learning component 104 can modify the set of medical images through at least one affine transformation for the data augmentation associated with the medical imaging data. In another embodiment, the machine learning component 104 can perform an inference phase. For example, the medical imaging data can be a medical image for an anatomical region of a patient associated with the medical image. Furthermore, the machine learning component 104 can perform the training phase for the machine learning process based on the medical image. For an inference phase associated with the machine learning component 104, the machine learning component 104 can generate learned medical imaging output regarding an anatomical region based on the convolutional neural network that receives medical imaging data.

In an aspect, the machine learning component 104 can employ a spring network of convolutional layers. The machine learning component 104 can employ the spring network of convolutional layers to generate the learned medical imaging output based on the medical imaging data. In an aspect, the machine learning component 104 can generate the learned medical imaging output based on a first convolutional layer process associated with sequential downsampling of the medical imaging data and a second convolutional layer process associated with sequential upsampling of the medical imaging data. The spring network of convolutional layers can include the first convolutional layer process associated with the sequential downsampling and the second convolutional layer process associated with sequential upsampling. In one example, the machine learning component 104 can perform a plurality of sequential downsampling and upsampling of the medical imaging data associated with convolutional layers of the convolutional neural network. The spring network of convolutional layers employed by the machine learning component 104 can alter convolutional layer filters similar to functionality of a spring. For instance, the machine learning component 104 can analyze the medical imaging data based on a first convolutional layer filter that comprises a first size, a second convolutional layer filter that comprises a second size that is different than the first size, and a third convolutional layer filter that comprises the first size associated with the first convolutional layer filter.

In certain embodiments, the machine learning component 104 can extract information that is indicative of correlations, inferences and/or expressions from the medical imaging data based on the spring network of convolutional layers. The machine learning component 104 can generate the learned medical imaging output based on the execution of at least one machine learning model associated with the spring network of convolutional layers. The learned medical imaging output generated by the machine learning component 104 can include, for example, learning, correlations, inferences and/or expressions associated with the medical imaging data. In an aspect, the machine learning component 104 can perform learning with respect to the medical imaging data explicitly or implicitly using the spring network of convolutional layers. The machine learning component 104 can also employ an automatic classification system and/or an automatic classification process to facilitate analysis of the medical imaging data. For example, the machine learning component 104 can employ a probabilistic and/or statistical-based analysis (e.g., factoring into the analysis utilities and costs) to learn and/or generate inferences with respect to the medical imaging data. The machine learning component 104 can employ, for example, a support vector machine (SVM) classifier to learn and/or generate inferences for medical imaging data. Additionally or alternatively, the machine learning component 104 can employ other classification techniques associated with Bayesian networks, decision trees and/or probabilistic classification models. Classifiers employed by the machine learning component 104 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, $x=(x1, x2, x3, x4, xn)$, to a confidence that the input belongs to a class—that is, $f(x)=\text{confidence}(\text{class})$.

To facilitate localization of one or more diseases associated with the medical imaging data, the machine learning component 104 can perform a local pooling process for an activation map associated with a convolutional layer of the convolutional neural network prior to performing a global pooling process associated with the convolutional neural network. Additionally or alternatively, the machine learning component 104 can generate the learned medical imaging output based on a class activation mapping process that applies a set of weights to a set of heat maps associated with the medical imaging data. Additionally or alternatively, the machine learning component 104 can process the medical imaging data based on one or more regularization techniques to classify one or more portions of the medical imaging data. In an aspect, the machine learning component 104 can also merge a set of classifier layers associated with the convolutional neural network and a set of activation maps associated with the convolutional neural network to generate the learned medical imaging output.

The medical imaging diagnosis component 106 can employ information provided by the machine learning component 104 (e.g., the learned medical imaging output) to classify and/or localize a disease associated with the medical imaging data. In an embodiment, the medical imaging diagnosis component 106 can determine a classification and an associated localization for a portion of the anatomical region based on the learned medical imaging output associated with the convolutional neural network. In certain embodiments, the medical imaging diagnosis component 106 can determine one or more confidence scores for the classification and/or the localization. For example, a first portion of the anatomical region with a greatest likelihood of a disease can be assigned a first confidence score, a second portion of the anatomical region with a lesser degree of likelihood of a disease can be assigned a second confidence score, etc. A disease classified and/or localized by the medical imaging diagnosis component 106 can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of disease associated with an anatomical region of a patient body. In an aspect, the medical imaging diagnosis component 106 can determine a prediction for a disease associated with the medical imaging data. For example, the medical imaging diagnosis component 106 can determine a probability score for a disease associated with the medical imaging data (e.g., a first percentage value representing likelihood of a negative prognosis for the disease and a second value representing a likelihood of a positive prognosis for the disease).

The visualization component 108 can generate deep learning data (e.g., DEEP LEARNING DATA shown in FIG. 1) based on the classification and/or the localization for the portion of the anatomical region. In an embodiment, the deep learning data can include a classification and/or a location for one or more diseases located in the medical imaging data. In certain embodiments, the deep learning data can include probability data indicative of a probability for one or more diseases being located in the medical imaging data. The probability data can be, for example, a probability array of data values for one or more diseases being located in the medical imaging data. In another embodiment, the visualization component 108 can generate a multi-dimensional visualization associated with the classification and/or the localization for the portion of the anatomical region. The multi-dimensional visualization can be a graphical representation of the medical imaging data that shows a classification and/or a location of one or more diseases with respect to a patient body. The visualization component 108 can also generate a display of the multi-dimensional visualization of the diagnosis provided by the medical imaging diagnosis component 106. For example, the visualization component 108 can render a 2D visualization of the portion of the anatomical region on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. In an aspect, the multi-dimensional visualization can include the deep learning data. The deep learning data associated with the multi-dimensional visualization can be indicative of a visual representation of the classification and/or the localization for the portion of the anatomical region. The deep learning data can also be rendered on the 3D model as one or more dynamic visual elements. In an aspect, the visualization component 108 can alter visual characteristics (e.g., color, size, hues, shading, etc.) of at least a portion of the deep learning data associated with the multi-dimensional visualization based on the classification and/or the localization for the portion of the anatomical region. For example, the classification and/or the localization for the portion of the anatomical region can be presented as different visual characteristics (e.g., colors, sizes, hues or shades, etc.), based on a result of deep learning and/or medical imaging diagnosis by the machine learning component 104 and/or the medical imaging diagnosis component 106. In another aspect, the visualization component 108 can allow a user to zoom into or out with respect to the deep learning data associated with the multi-dimensional visualization. For example, the visualization component 108 can allow a user to zoom into or out with respect to a classification and/or a location of one or more diseases identified in the anatomical region of the patient body. As such, a user can view, analyze and/or interact with the deep learning data associated with the multi-dimensional visualization.

It is to be appreciated that technical features of the deep learning component 102 are highly technical in nature and not abstract ideas. Processing threads of the deep learning component 102 that process and/or analyze the medical imaging data, determine deep learning data, etc. cannot be performed by a human (e.g., are greater than the capability of a single human mind). For example, the amount of the medical imaging data processed, the speed of processing of the medical imaging data and/or the data types of the medical imaging data processed by the deep learning component 102 over a certain period of time can be respectively greater, faster and different than the amount, speed and data type that can be processed by a single human mind over the same period of time. Furthermore, the medical imaging data processed by the deep learning component 102 can be one or more medical images generated by sensors of a medical imaging device. Moreover, the deep learning component 102 can be fully operational towards performing one or more other functions (e.g., fully powered on, fully executed, etc.) while also processing the medical imaging data.

Figure 2:
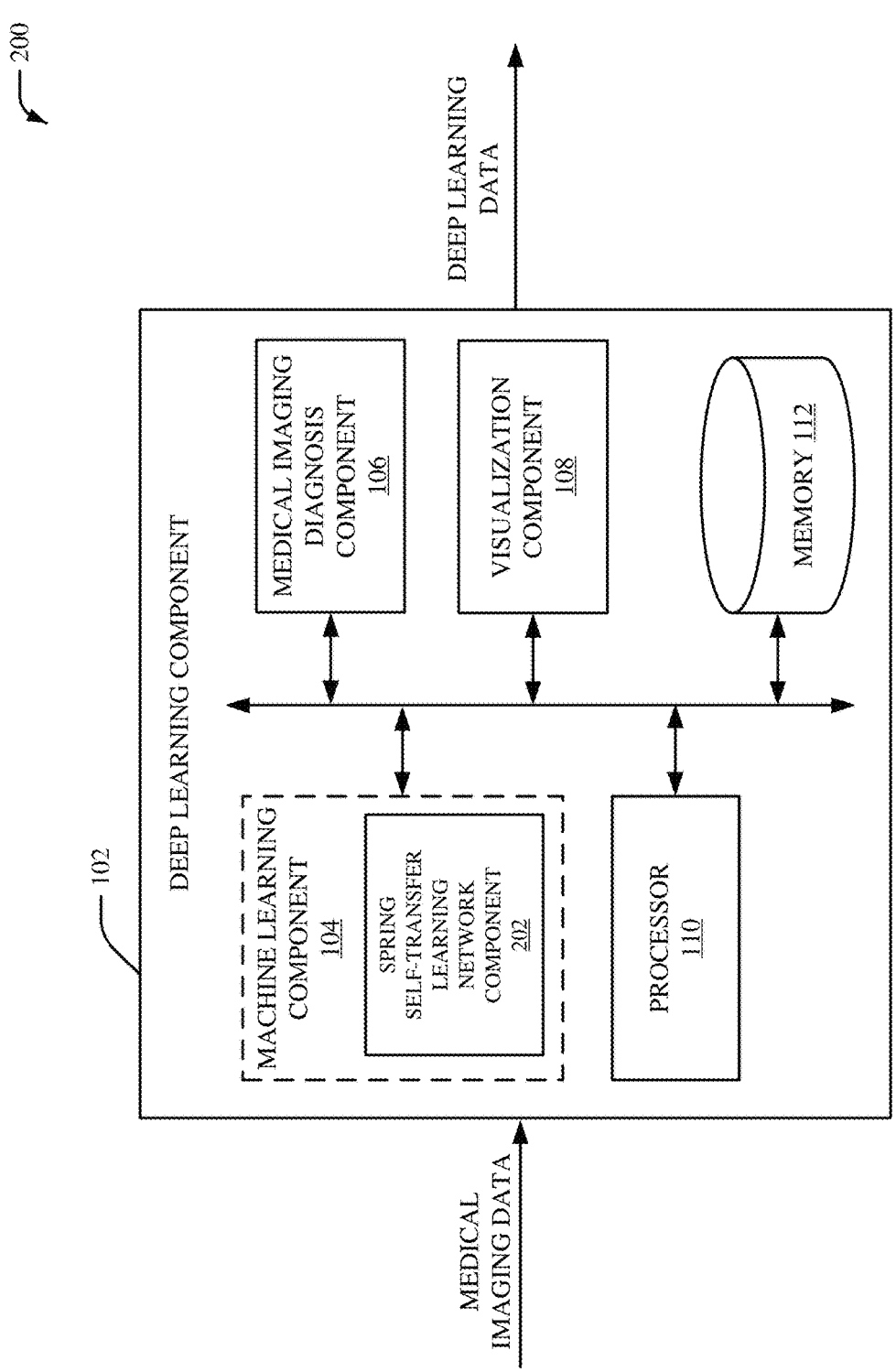

Referring now to FIG. 2, there is illustrated a non-limiting implementation of a system 200 in accordance with various aspects and implementations of this disclosure. Repetitive description of like elements employed in other embodiments described herein is omitted for sake of brevity. The system 200 can include the deep learning component 102, and the deep learning can include the machine learning component 104, the medical imaging diagnosis component 106, the visualization component 108, the processor 110 and/or the memory 112. The machine learning component 104 can include a spring self-transfer learning (STL) network component 202.

The spring STL network component 202 can provide a weakly supervised framework with self-transfer learning. For instance, a convolutional neural network model employed by the spring STL network component 202 can be pre-trained using a set of medical images formatted as image-level labels (e.g., weak-labeled images) without location information with respect to localization of one or more features of the set of medical images. The convolutional neural network model employed by the spring STL network component 202 can employ a plurality of sequential downsampling and upsampling of the medical imaging data received by the spring STL network component 202. For example, the plurality of sequential downsampling and upsampling can be performed by shared spring convolutional layers that behave in a spring-like manner. The shared spring convolutional layers can include convolutional layer filters with various sizes. Furthermore, one or more convolutional layer filters from the shared spring convolutional layers can be repeated. In an aspect, the spring STL network component 202 can generate learned medical imaging output associated with the medical imaging data based on the shared spring convolutional layers. The spring STL network component 202 can additionally employ classification layers and/or localization layers to generate the learned medical imaging output. For instance, the learned medical imaging output generated by the spring STL network component 202 can include one or more classifications for the medical imaging data that is determined based on the shared spring convolutional layers and the classification layers. Additionally or alternatively, the learned medical imaging output generated by the spring STL network component 202 can include one or more localizations for the medical imaging data that is determined based on the shared spring convolutional layers and the localization layers.

Figure 3:
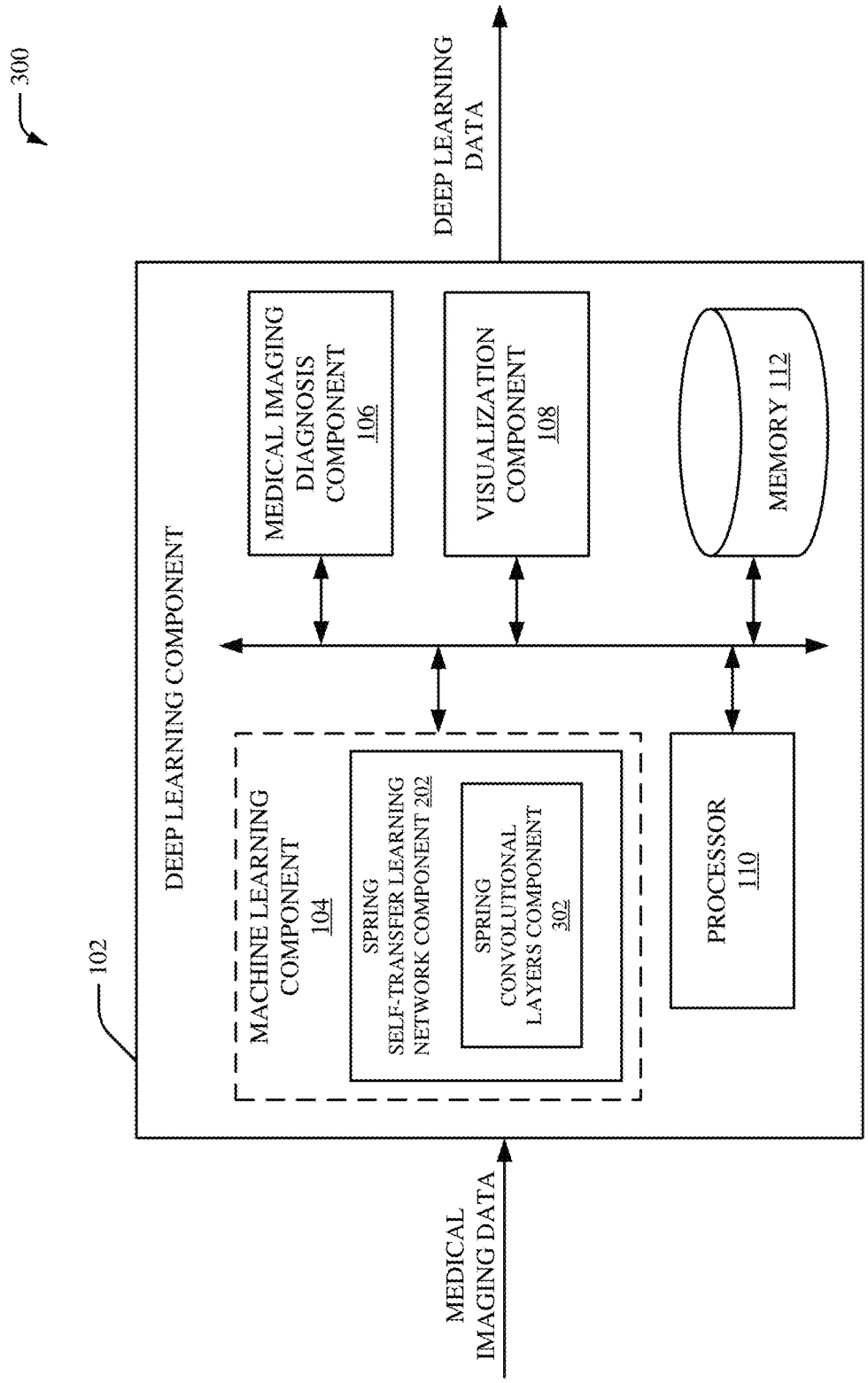

Referring now to FIG. 3, there is illustrated a non-limiting implementation of a system 300 in accordance with various aspects and implementations of this disclosure. Repetitive description of like elements employed in other embodiments described herein is omitted for sake of brevity. The system 300 can include the deep learning component 102, and the deep learning can include the machine learning component 104, the medical imaging diagnosis component 106, the visualization component 108, the processor 110 and/or the memory 112. The machine learning component 104 can include the spring STL network component 202. The spring STL network component 202 can include a spring convolutional layers component 302.

The spring convolutional layers component 302 can execute the shared spring convolutional layers. The shared spring convolutional layers can be associated with a machine learning convolutional layer process. The shared spring convolutional layers executed by the spring convolutional layers component 302 can behave in a spring-like manner. For example, the shared spring convolutional layers executed by the spring convolutional layers component 302 can include convolutional layer filters with various sizes. Furthermore, one or more convolutional layer filters from the shared spring convolutional layers executed by the spring convolutional layers component 302 can be repeated. For instance, shared spring convolutional layers executed by the spring convolutional layers component 302 can include a first convolutional layer filter that comprises a first size, a second convolutional layer filter that comprises a second size that is different than the first size, a third convolutional layer filter that comprises the first size associated with the first convolutional layer filter, etc. In an aspect, spring convolutional layers component 302 can extract feature information from the medical imaging data using the shared spring convolutional layers. The feature information can include, for example, a set of data matrices (e.g., a set of feature maps) extracted from the medical imaging data. A size of the set of data matrices can be smaller than a size of a data matrix associated with the medical imaging data.

Figure 4:
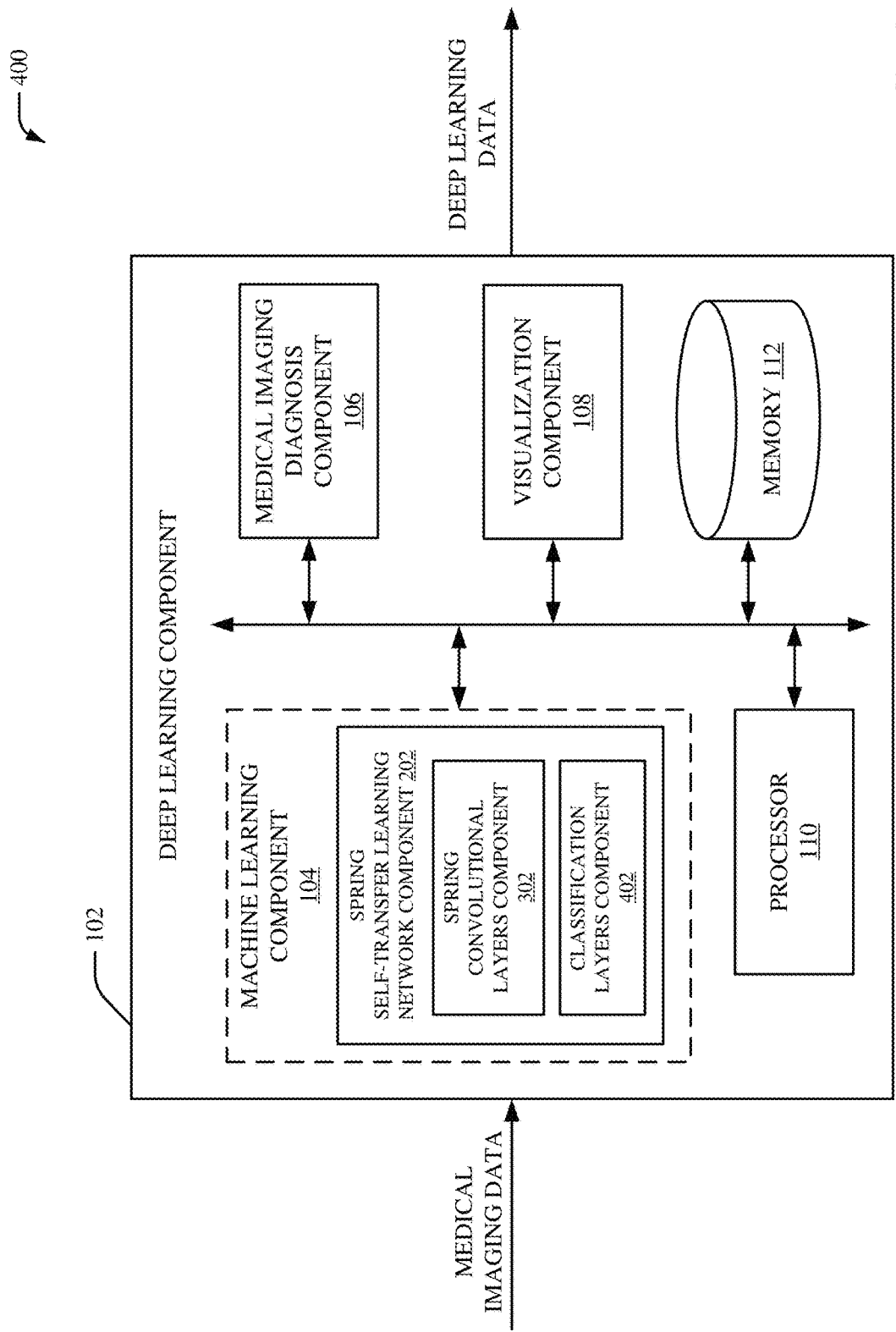

Referring now to FIG. 4, there is illustrated a non-limiting implementation of a system 400 in accordance with various aspects and implementations of this disclosure. Repetitive description of like elements employed in other embodiments described herein is omitted for sake of brevity. The system 400 can include the deep learning component 102, and the deep learning can include the machine learning component 104, the medical imaging diagnosis component 106, the visualization component 108, the processor 110 and/or the memory 112. The machine learning component 104 can include the spring STL network component 202. The spring STL network component 202 can include the spring convolutional layers component 302 and/or a classification layers component 402.

The classification layers component 402 can be a classifier that performs a classification process to classify the medical imaging data. The classification layers component 402 can employ a set of classification layers (e.g., a set of fully connected layers) to perform the classification process. For instance, the classification layers component 402 can classify the medical imaging data into a class based on the set of classification layers (e.g., the set of fully connected layers). The classification layers component 402 can also employ a training dataset to facilitate the classification of the medical imaging data. For instance, the classification layers component 402 can also classify the medical imaging data into the class based on the training dataset. The training dataset can be generated during a training phase that trains the convolutional neural network model employed by the spring convolutional layers component 302. In an embodiment, the classification layers component 402 can employ an automatic classification system and/or an automatic classification process to facilitate analysis of the medical imaging data. For example, the classification layers component 402 can employ a probabilistic and/or statistical-based analysis (e.g., factoring into the analysis utilities and costs) to learn and/or generate inferences with respect to the medical imaging data. The classification layers component 402 can employ, for example, a support vector machine (SVM) classifier to learn and/or generate inferences for medical imaging data. Additionally or alternatively, the classification layers component 402 can employ other classification techniques associated with Bayesian networks, decision trees and/or probabilistic classification models. Classifiers employed by the classification layers component 402 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, $x=(x1, x2, x3, x4, xn)$, to a confidence that the input belongs to a class— that is, $f(x)=confidence(class)$.

Figure 5:
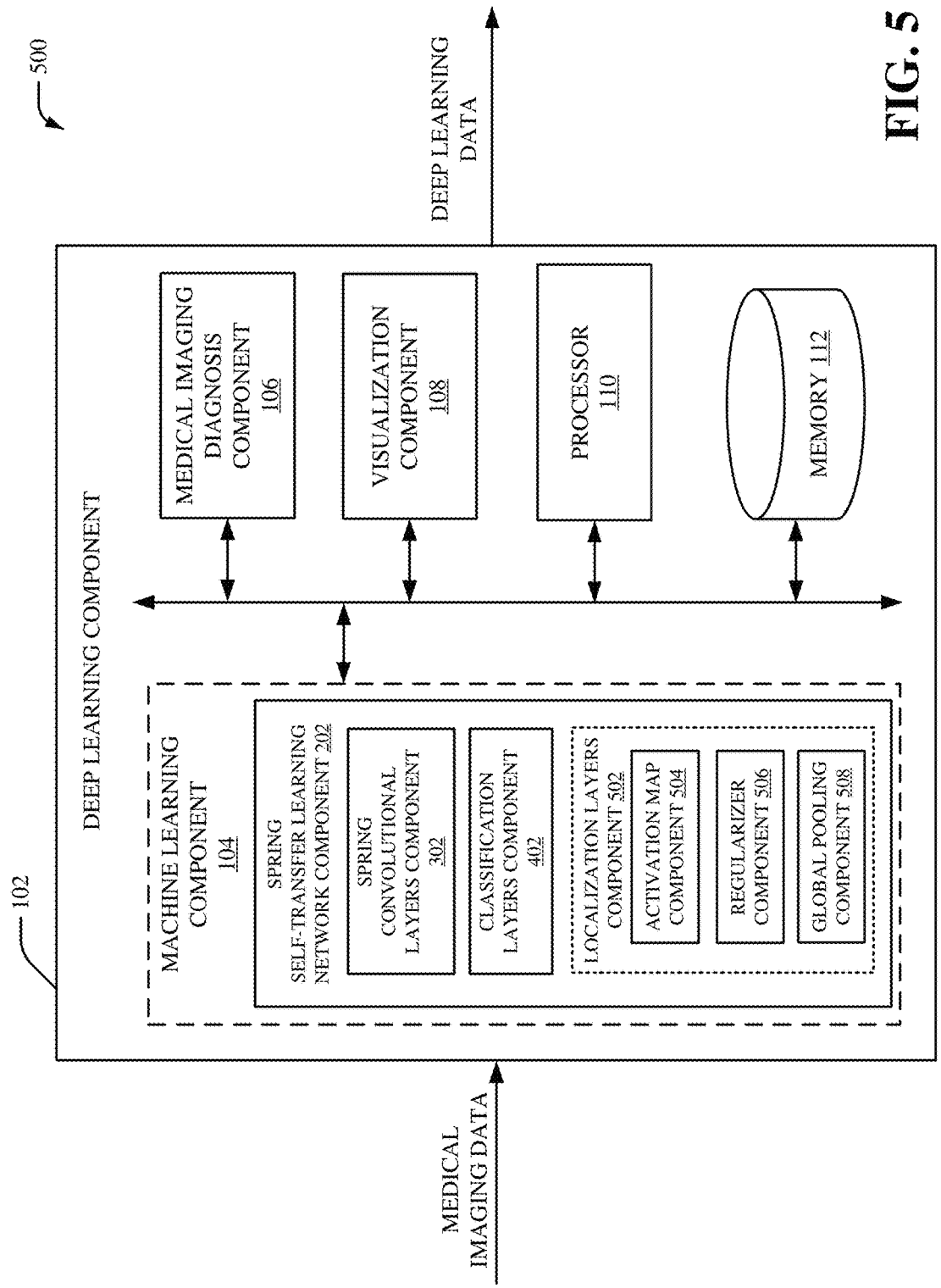

Referring now to FIG. 5, there is illustrated a non-limiting implementation of a system 500 in accordance with various aspects and implementations of this disclosure. Repetitive description of like elements employed in other embodiments described herein is omitted for sake of brevity. The system 500 can include the deep learning component 102, and the deep learning can include the machine learning component 104, the medical imaging diagnosis component 106, the visualization component 108, the processor 110 and/or the memory 112. The machine learning component 104 can include the spring STL network component 202. The spring STL network component 202 can include the spring convolutional layers component 302, the classification layers component 402 and/or a localization layers component 502. The localization layers component 502 can include an activation map component 504, a regularizer component 506 and/or a global pooling component 508.

The localization layers component 502 can be a localizer that performs a localization process to localize one or more classifications of the medical imaging data. The localization layers component 502 can employ a set of localization layers to perform the localization process. For instance, the localization layers component 502 can localize a classification of the medical imaging data based on the set of localization layers. In an embodiment, the activation map component 504 can generate a set of activation maps. The set of activation maps can be score maps for each class associated with the classification layers component 402. For instance, a number of activation maps included in the set of activation maps can correspond to a number of classes determined by the classification layers component 402. In another embodiment, the regularizer component 506 can be employed to reduce overfitting associated with the set of activation maps. The regularizer component 506 can perform a local pooling process that reduces dimensionality of the set of activation maps. For example, the regularizer component 506 can include a local pooling layer to reduce singularity issues and/or to improve localization for the localization layers component 502. In yet another embodiment, the global pooling component 508 can perform a global pooling process that further reduces dimensionality of the set of activation maps. In an aspect, a size of a filter associated with the global pooling process can be larger than a size of a filter associated with the local pooling layer. In one example, a size of a filter associated with the global pooling process can correspond to a size of the medical imaging data.

Figure 6:
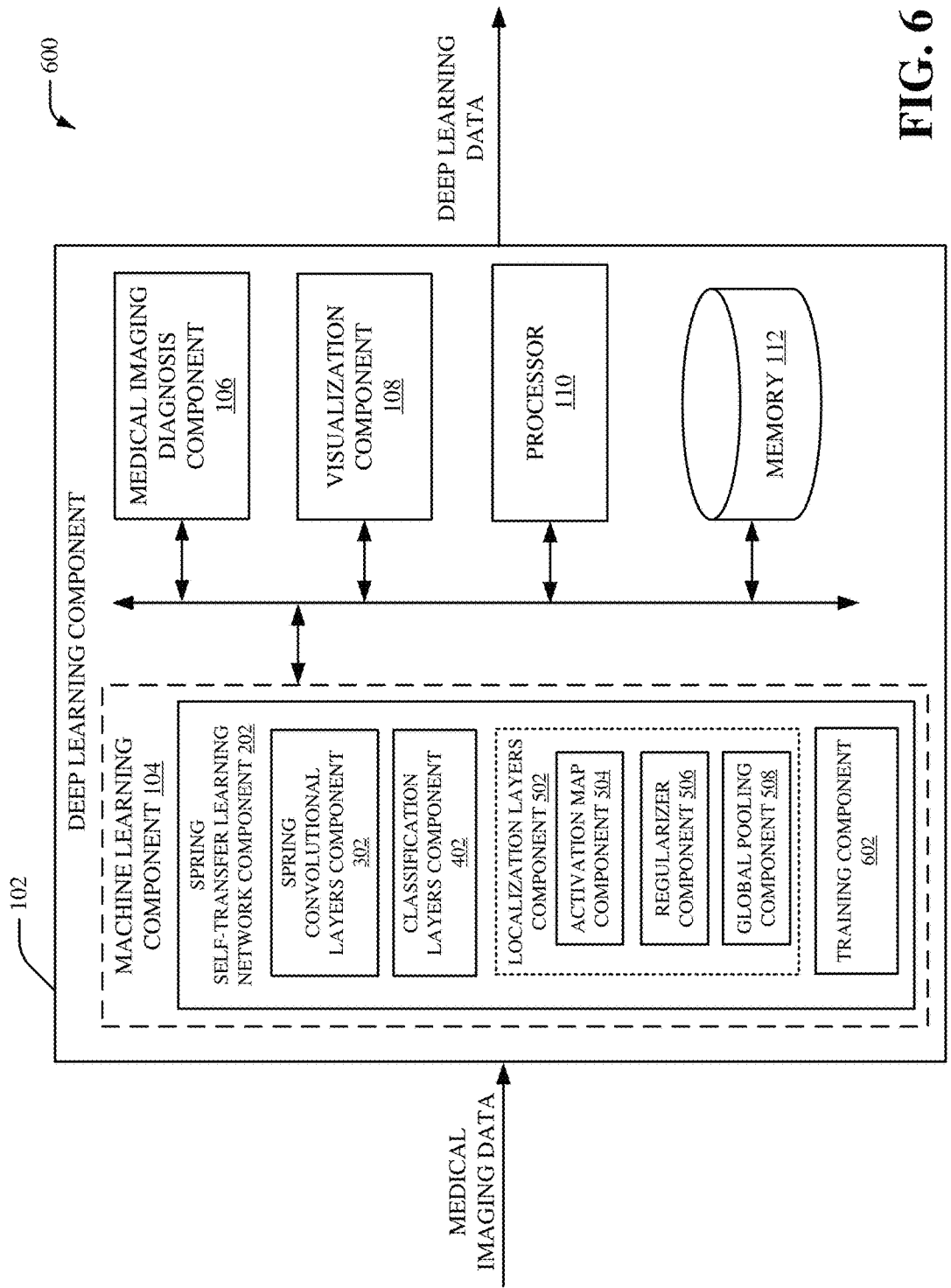

Referring now to FIG. 6, there is illustrated a non-limiting implementation of a system 600 in accordance with various aspects and implementations of this disclosure. Repetitive description of like elements employed in other embodiments described herein is omitted for sake of brevity. The system 600 can include the deep learning component 102, and the deep learning can include the machine learning component 104, the medical imaging diagnosis component 106, the visualization component 108, the processor 110 and/or the memory 112. The machine learning component 104 can include the spring STL network component 202. The spring STL network component 202 can include the spring convolutional layers component 302, the classification layers component 402, the localization layers component 502 and/or a training component 602. The localization layers component 502 can include the activation map component 504, the regularizer component 506 and/or the global pooling component 508.

The training component 602 can perform a training phase for a neural network model employed by the spring convolutional layers component 302. For example, the medical imaging data can be a set of medical images (e.g., a set of x-ray images, etc.) stored in a data store. Furthermore, the training component 602 can perform the training phase for a neural network model (e.g., a convolutional neural network model) based on the set of medical images stored in a data store to train the neural network model. In an embodiment, training component 602 can train a convolutional neural network (e.g., the neural network model) by performing iterative sequential downsampling and upsampling of the medical imaging data associated with convolutional layers of the convolutional neural network. In an aspect, the training component 602 can generate a set of filter values for the convolutional neural network (e.g., the neural network model) based on the iterative sequential downsampling and upsampling of the medical imaging data. For example, the training component 602 can generate a set of as set of weights for a set of filters associated with the convolutional neural network (e.g., the neural network model) based on the iterative sequential downsampling and upsampling of the medical imaging data. In certain embodiments, the training component 602 can analyze the medical imaging data based on a first convolutional layer filter that comprises a first size, analyze the medical imaging database on a second convolutional layer filter that comprises a second size that is different than the first size, analyze the medical imaging database on a third convolutional layer filter that comprises the first size associated with the first convolutional layer filter, etc.

Figure 7:
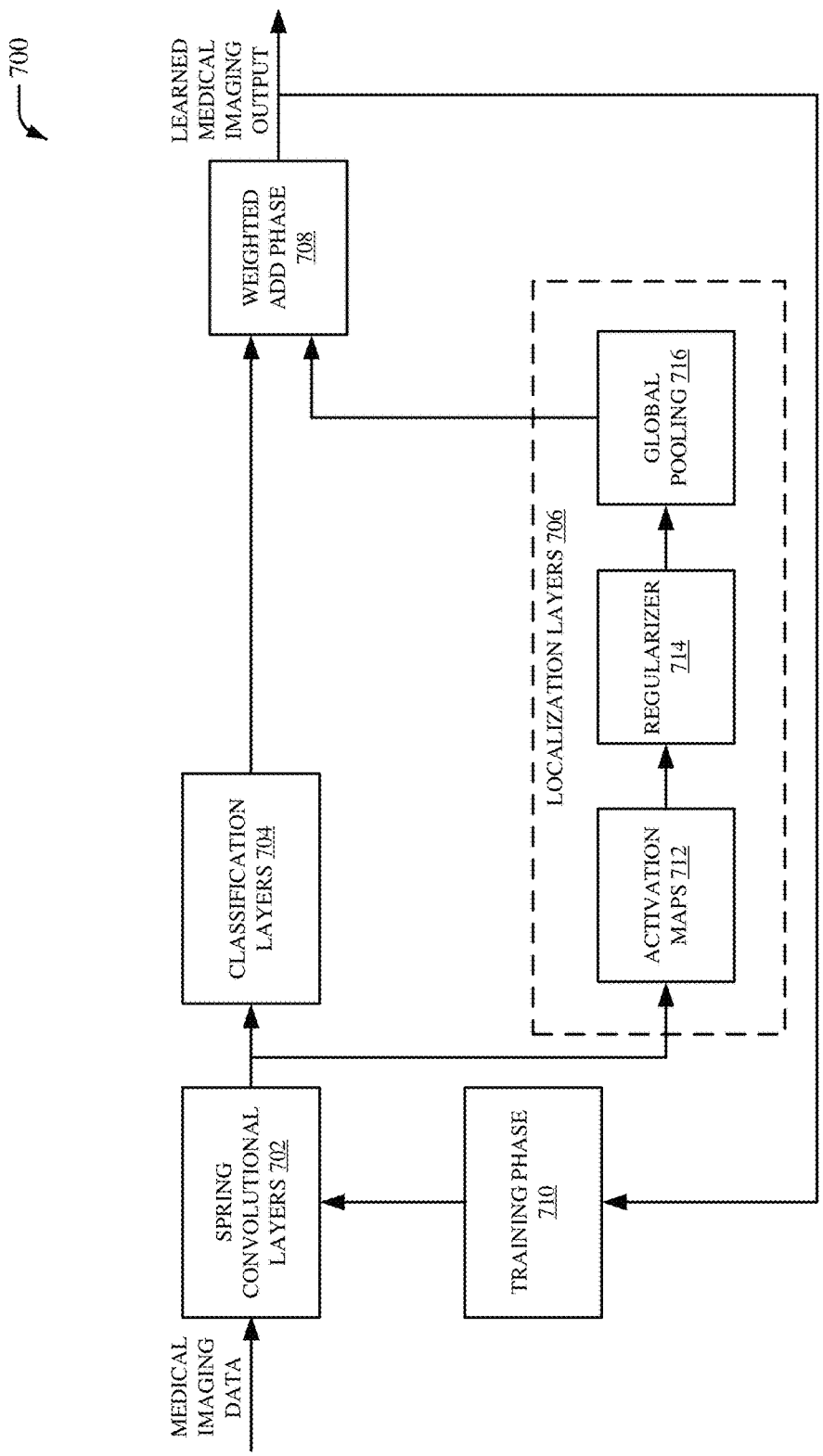
FIG. 7 illustrates an example system associated with a spring self-transfer learning network, in accordance with various aspects and implementations described herein.

Referring now to FIG. 7, there is illustrated a non-limiting implementation of a system 700 in accordance with various aspects and implementations of this disclosure. Repetitive description of like elements employed in other embodiments described herein is omitted for sake of brevity. The system 700 can include spring convolutional layers 702, classification layers 704, localization layers 706, a weighted add phase 708 and/or a training phase 710. The localization layers 706 can include activation maps 712, a regularizer 714 and/or global pooling 716.

The system 700 can be, for example, a spring self-transfer learning network. The spring convolutional layers 702 can receive the medical imaging data. In an embodiment, the spring convolutional layers 702 can be executed by the spring convolutional layers component 302. The spring convolutional layers 702 can behave in a spring-like manner. For example, spring convolutional layers 702 can include convolutional layer filters with various sizes. Furthermore, one or more convolutional layer filters from the spring convolutional layers 702 can be repeated. For instance, the spring convolutional layers 702 can include a first convolutional layer filter that comprises a first size, a second convolutional layer filter that comprises a second size that is different than the first size, a third convolutional layer filter that comprises the first size associated with the first convolutional layer filter, etc. In an aspect, the spring convolutional layers 702 can extract feature information from the medical imaging data. The feature information can include, for example, a set of data matrices (e.g., a set of feature maps) extracted from the medical imaging data. A size of the set of data matrices can be smaller than a size of a data matrix associated with the medical imaging data.

The classification layers 704 can further process the feature information extracted from the spring convolutional layers 702. In an embodiment, the classification layers 704 can be executed by the classification layers component 402. The classification layers 704 can determine one or more classifications for the medical imaging data. In an aspect, each CNN neuron in a first layer (e.g., a previous layer) from the classification layers 704 can be connected to each neuron in a second layer (e.g., a next layer) from the classification layers 704. In another aspect, the one or more classifications for the medical imaging data can be received by the weighted add phase 708.

The localization layers 706 can also further process the feature information extracted from the spring convolutional layers 702. In an embodiment, the localization layers 706 can be executed by the localization layers component 502. The localization layers 706 can determine one or more localizations for the medical imaging data. In an aspect, the localization layers 706 can employ the activation maps 712, the regularizer 714 and/or the global pooling 716 to determine the one or more localizations for the medical imaging data. In an embodiment, the activation maps 712 can be executed by the activation map component 504, the regularizer 714 can correspond to the regularizer component 506, and/or the global pooling 716 can be performed by the global pooling component 508. The activation maps 712 can be score maps (e.g., class activation maps) for each class associated with the spring convolutional layers 702. For instance, a number of the activation maps 712 can correspond to a number of classes associated with the spring convolutional layers 702.

The regularizer 714 can reduce overfitting associated with the activation maps 712. The regularizer 714 can be, for example, a local pooling process that reduces dimensionality of the activation maps 712. For example, the regularizer 714 can include a local pooling layer that reduces dimensionality of the activation maps 712. The global pooling 716 can be a global pooling process that further reduces dimensionality of the activation maps 712. In an aspect, a size of a filter associated with the global pooling 716 can be larger than a size of a filter associated with the regularizer 714. In one example, a size of a filter associated with the global pooling 716 can correspond to a size of the medical imaging data received by the spring convolutional layers 702. As such, the regularizer 714 (e.g., a local pooling layer associated with the regularizer 714) can be performed prior to the global pooling 716 with respect to the activation maps 712 to, for example, overcome one or more singularity issues and/or to improve localization by the localization layers 706. In an aspect, the one or more localizations for the medical imaging data can be received by the weighted add phase 708. The weighted add phase 708 can combine the one or more classifications and the one or more localizations to generate the learned medical imaging output. For example, the learned medical imaging output can provide a classification and/or a location for one or more features associated with the medical imaging data.

In certain embodiments, the system 700 can employ the training phase 710. The training phase 710 can perform a training phase for a neural network model employed by the spring convolutional layers 702. For example, the medical imaging data can be a set of medical images (e.g., a set of x-ray images, etc.) stored in a data store. Furthermore, the training phase 710 can perform the training phase for a neural network model (e.g., a convolutional neural network model) based on the set of medical images stored in a data store to train the neural network model. In an embodiment, training phase 710 can train a convolutional neural network (e.g., the neural network model) by performing iterative sequential downsampling and upsampling of the medical imaging data associated with convolutional layers of the convolutional neural network. In an aspect, the training phase 710 can generate a set of filter values for the convolutional neural network (e.g., the neural network model) based on the iterative sequential downsampling and upsampling of the medical imaging data. For example, the training phase 710 can generate a set of as set of weights for a set of filters associated with the convolutional neural network (e.g., the neural network model) based on the iterative sequential downsampling and upsampling of the medical imaging data. In an embodiment, the training phase 710 can analyze the medical imaging data based on a first convolutional layer filter that comprises a first size, analyze the medical imaging database on a second convolutional layer filter that comprises a second size that is different than the first size, analyze the medical imaging database on a third convolutional layer filter that comprises the first size associated with the first convolutional layer filter, etc.

Figure 8:
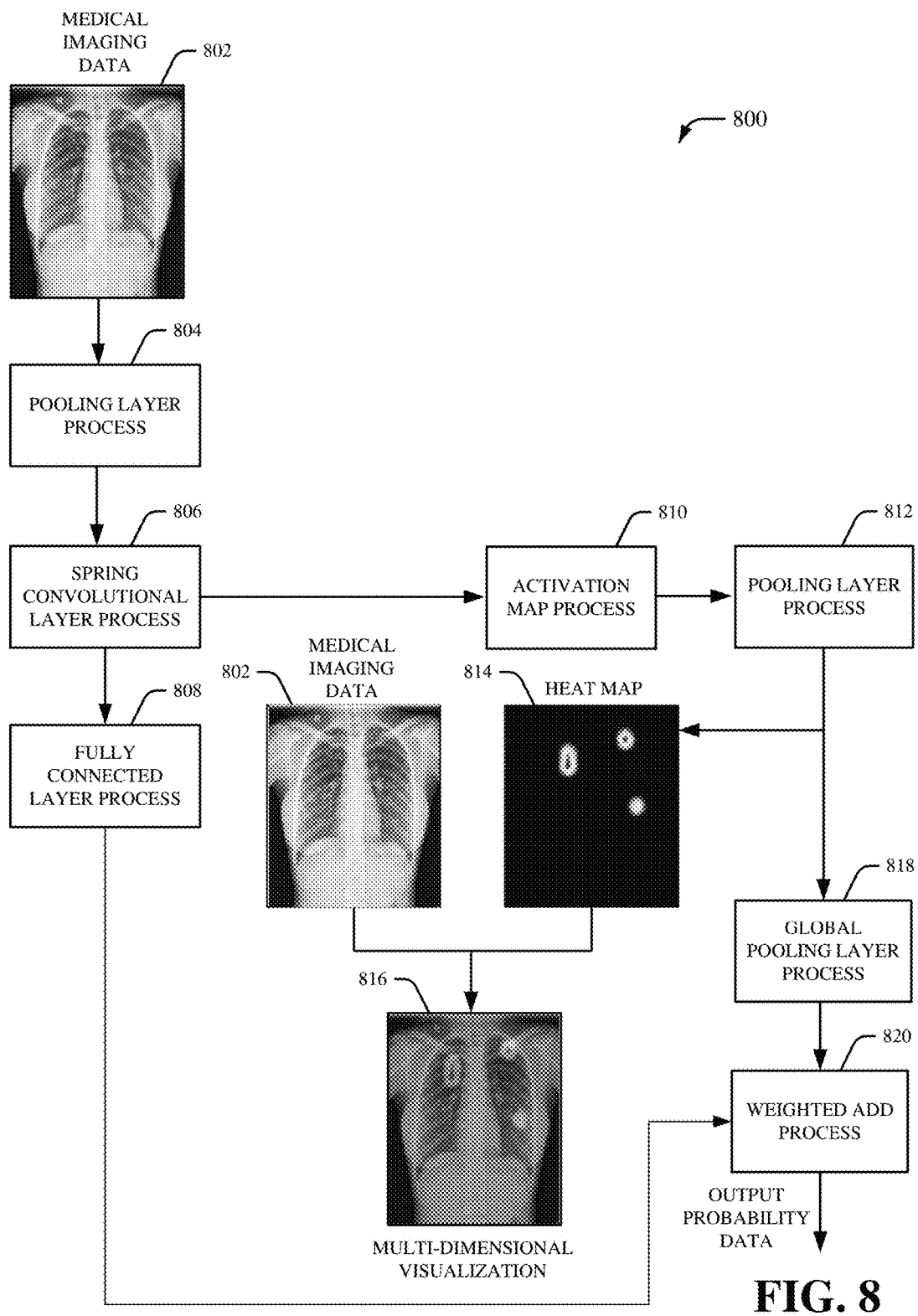
FIG. 8 illustrates an example system associated with an inference phase for a spring self-transfer learning network, in accordance with various aspects and implementations described herein.

Referring now to FIG. 8, there is illustrated a non-limiting implementation of a system 800 in accordance with various aspects and implementations of this disclosure. Repetitive description of like elements employed in other embodiments described herein is omitted for sake of brevity. The system 800 can be associated with an inference phase for a spring self-transfer learning network. The system 800 can include medical imaging data 802 that is received by a pooling layer process 804. In an embodiment, the medical imaging data 802 can correspond to the medical imaging data received by the deep learning component 102. The medical imaging data 802 can be, for example, two-dimensional medical imaging data and/or three-dimensional medical imaging data generated by a medical imaging device. For instance, the medical imaging data 802 can be electromagnetic radiation imagery captured via a set of sensors (e.g., a set of sensors associated with a medical imaging device). In one example, the medical imaging data 802 can be an x-ray image. The pooling layer process 804 can format the medical imaging data 802 for processing by the spring convolutional layer process 806. For example, the pooling layer process 804 can convert the medical imaging data 802 into a data matrix with a particular size. In certain embodiments, the pooling layer process 804 can reduce dimensionality of the medical imaging data 802. For example, the pooling layer process 804 can reduce the particular size of the data matrix. The pooling layer process 804 can be followed by a spring convolutional layer process 806. The spring convolutional layer process 806 can be a machine learning convolutional layer process. Furthermore, the spring convolutional layer process 806 can be, for example, a sequential convolutional layer process that behaves in a spring-like manner. The spring convolutional layer process 806 can include a plurality of sequential downsampling and upsampling of the medical imaging data 802. For example, the plurality of sequential downsampling and upsampling of the spring convolutional layer process 806 can be performed by shared spring convolutional layers that behave in a spring-like manner. The shared spring convolutional layers of the spring convolutional layer process 806 can include convolutional layer filters with various sizes. Furthermore, one or more convolutional layer filters from the shared spring convolutional layers of the spring convolutional layer process 806 can be repeated.

The spring convolutional layer process 806 can be followed by a fully connected layer process 808 implemented in parallel to an activation map process 810. The fully connected layer process 808 can be a machine learning classification process that classifies the medical imaging data 802. In an aspect, the fully connected layer process 808 can determine one or more classes for the medical imaging data 802. The activation map process 810 can generate a set of activation maps for the medical imaging data 802. For example, the set of activation maps generated by the activation map process 810 can be a set of score maps associated with the one or more classes determined by the fully connected layer process 808. In an aspect, a number of activation maps included in the set of activation maps can correspond to a number of classes determined by the fully connected layer process 808. The activation map process 810 can be followed by a pooling layer process 812. The pooling layer process 812 can reduce dimensionality of the set of activation maps generated by the activation map process 810.

A heat map 814 can be generated following the pooling layer process 812. The heat map 814 can include one or more localizations to localize one or more classifications of the medical imaging data 802. For example, the heat map 814 can be a graphical representation of data generated by the spring convolutional layer process 806 and/or the activation map process 810. The data generated by the spring convolutional layer process 806 and/or the activation map process 810 can be represented as different colors based on a value of the data. For example, one or more data values that satisfy a first defined criterion (e.g., one or more data values that represents a high degree of localization) can be represented as a red color, one or more data values that satisfy a second defined criterion (e.g., one or more data values that represents a medium degree of localization) can be represented as a green color, one or more data values that satisfy a third defined criterion (e.g., one or more data values that represents a low degree of localization) can be represented as a green color, etc. The heat map 814 can be combined with the medical imaging data 802 to generate a multi-dimensional visualization 816. The pooling layer process 812 can also be followed by a global pooling layer process 818. The global pooling layer process 818 can further alter dimensionality of the of the set of activation maps generated by the activation map process 810. For example, the global pooling layer process 818 alter dimensionality of the of the set of activation maps generated by the activation map process 810 to correspond to dimensionality of the medical imaging data 802. The global pooling layer process 818 can be followed by a weighted add process 820.

The fully connected layer process 808 can also be followed by the weighted add process 820. The weighted add process 820 can employ information from the spring convolutional layer process 806 (e.g., one or more localizations) and the fully connected layer process 808 (e.g., one or more classifications) to generate output probability data.

Figure 9:
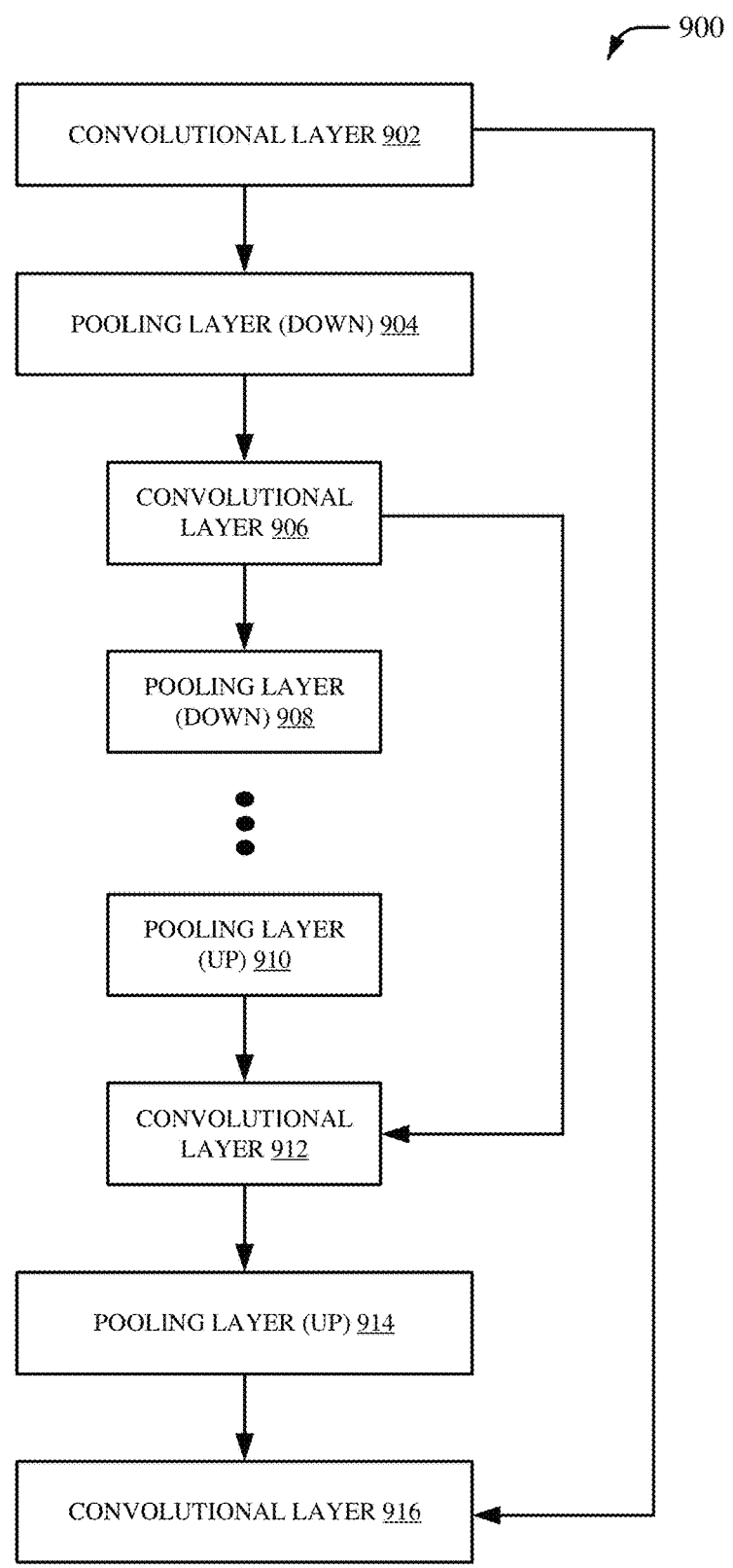
FIG. 9 illustrates an example system associated with sequential upsampling and downsampling for a spring self-transfer learning network, in accordance with various aspects and implementations described herein.

Referring now to FIG. 9, there is illustrated a non-limiting implementation of a system 900 in accordance with various aspects and implementations of this disclosure. Repetitive description of like elements employed in other embodiments described herein is omitted for sake of brevity. The system 900 can be associated with sequential upsampling and downsampling for a spring self-transfer learning network. In an embodiment, the system 900 can be associated with the spring convolutional layers component 302.

The system 900 can include a convolutional layer 902. The convolutional layer 902 can be a first convolutional layer of a convolutional neural network that processes medical imaging data. Furthermore, the convolutional layer 902 can be associated with a first filter size. The convolutional layer 902 can be followed by a pooling layer (down) 904. The pooling layer (down) 904 can be associated with downsampling. For instance, the pooling layer (down) 904 can reduce dimensionality of data generated by the convolutional layer 902. In one example, the pooling layer (down) 904 can reduce dimensionality of a feature map for medical imaging data processed by the convolutional layer 902. The pooling layer (down) 904 can be followed by a convolutional layer 906. The convolutional layer 906 can be a second convolutional layer of the convolutional neural network that processes the medical imaging data. Furthermore, the convolutional layer 906 can be associated with a second filter size that is different than the first filter size associated with the convolutional layer 902. For example, the second filter size associated with the convolutional layer 906 can be smaller than the first filter size associated with the convolutional layer 902. The convolutional layer 906 can be followed by a pooling layer (down) 908. The pooling layer (down) 908 can be associated with downsampling. For instance, the pooling layer (down) 908 can reduce dimensionality of data generated by the convolutional layer 906. In one example, the pooling layer (down) 908 can reduce dimensionality of a feature map for medical imaging data processed by the convolutional layer 906. The pooling layer (down) 908 can be followed by a convolutional layer (not shown), which, in turn, can be followed by a pooling layer (up) 910. However, in certain embodiments, the pooling layer (down) 910 can be followed by one or more other convolutional layers and/or one or more other pooling layers (down) prior to the pooling layer (up) 910 to further process medical imaging data with different filter sizes and/or further reduction to dimensionality of data. The pooling layer (up) 910 can be associated with upsampling. For instance, the pooling layer (up) 910 can increase dimensionality of data generated by one or more convolutional layers. In one example, the pooling layer (up) 910 can increase dimensionality of a feature map for medical imaging data processed by one or more convolutional layers. The pooling layer (up) 910 can be followed by a convolutional layer 912. The convolutional layer 912 can be, for example, a third convolutional layer of the convolutional neural network that processes the medical imaging data. Furthermore, the convolutional layer 912 can be associated with the second filter size associated with the convolutional layer 906.

The convolutional layer 912 can be followed by a pooling layer (up) 914. The pooling layer (up) 914 can be associated with upsampling. For instance, the pooling layer (up) 914 can increase dimensionality of data generated by the convolutional layer 912. In one example, the pooling layer (up) 914 can increase dimensionality of a feature map for medical imaging data processed by the convolutional layer 912. The pooling layer (up) 914 can be followed by a convolutional layer 916. The convolutional layer 916 can be, for example, a fourth convolutional layer of the convolutional neural network that processes the medical imaging data. Furthermore, the convolutional layer 916 can be associated with the first filter size associated with the convolutional layer 912. As such, the system 900 can behave similar to functionality of a spring where a filter size for one or more convolutional layers are repeated while processing medical imaging data via a convolutional neural network.

Figure 10:
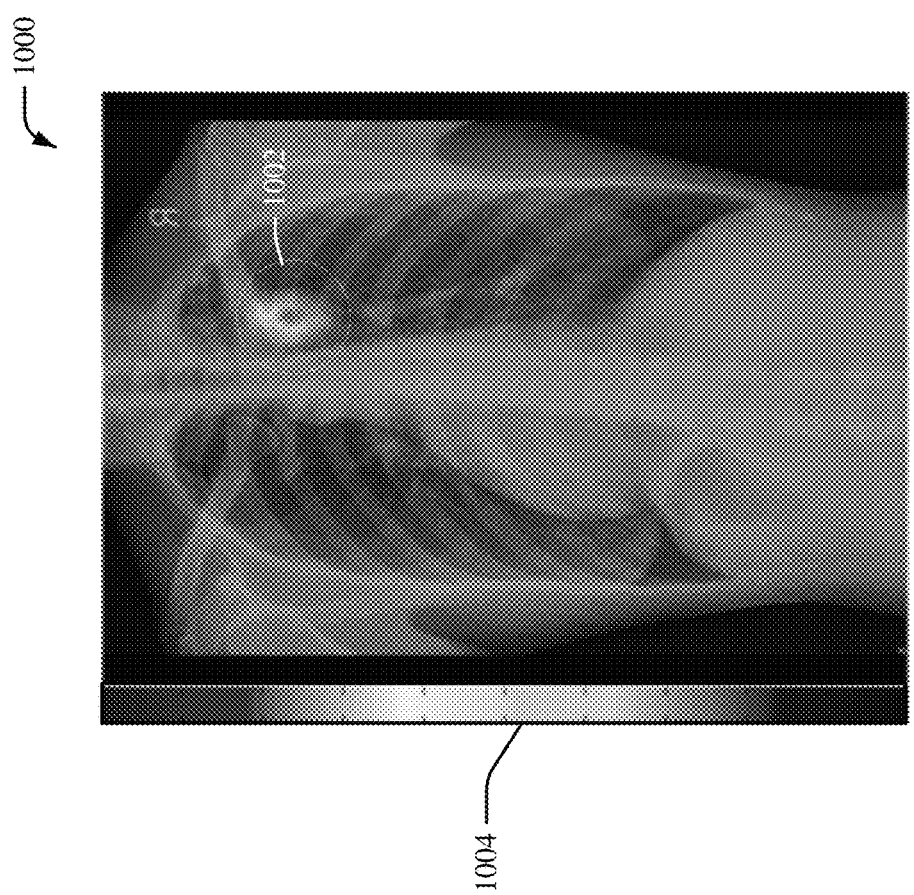
FIG. 10 illustrates an example multi-dimensional visualization, in accordance with various aspects and implementations described herein.

FIG. 10 illustrates an example multi-dimensional visualization 1000, in accordance with various aspects and implementations described herein. The multi-dimensional visualization 1000 can, for example, display a medical imaging diagnosis for a patient. For example, the multi-dimensional visualization 1000 can display one or more classifications and/or one or more localizations for one or more diseases identified in medical imaging data. In an aspect, the multi-dimensional visualization 1000 can include localization data 1002 for a medical imaging diagnosis. The localization data 1002 can be a predicted location for a disease associated with medical imaging data processed by the machine learning component 104 and/or the medical imaging diagnosis component 106. Visual characteristics (e.g., a color, a size, hues, shading, etc.) of the localization data 1002 can be dynamic based on information provided by the machine learning component 104 and/or the medical imaging diagnosis component 106. For instance, a first portion of the localization data 1002 can comprise a first visual characteristic, a second portion of the localization data 1002 can comprise a second visual characteristic, a third portion of the localization data 1002 can comprise a third visual characteristic, etc. In an embodiment, a display environment associated with the multi-dimensional visualization 1000 can include a heat bar 1004. The heat bar 1004 can include a set of colors that correspond to different values for the localization data 1002. For example, a first color (e.g., a color red) in the heat bar 1004 can correspond to a first value for the localization data 1002, a second color (e.g., a color green) in the heat bar 1004 can correspond to a second value for the localization data 1002, a third color (e.g., a color blue) in the heat bar 1004 can correspond to a third value for the localization data 1002, etc.

Figure 11:
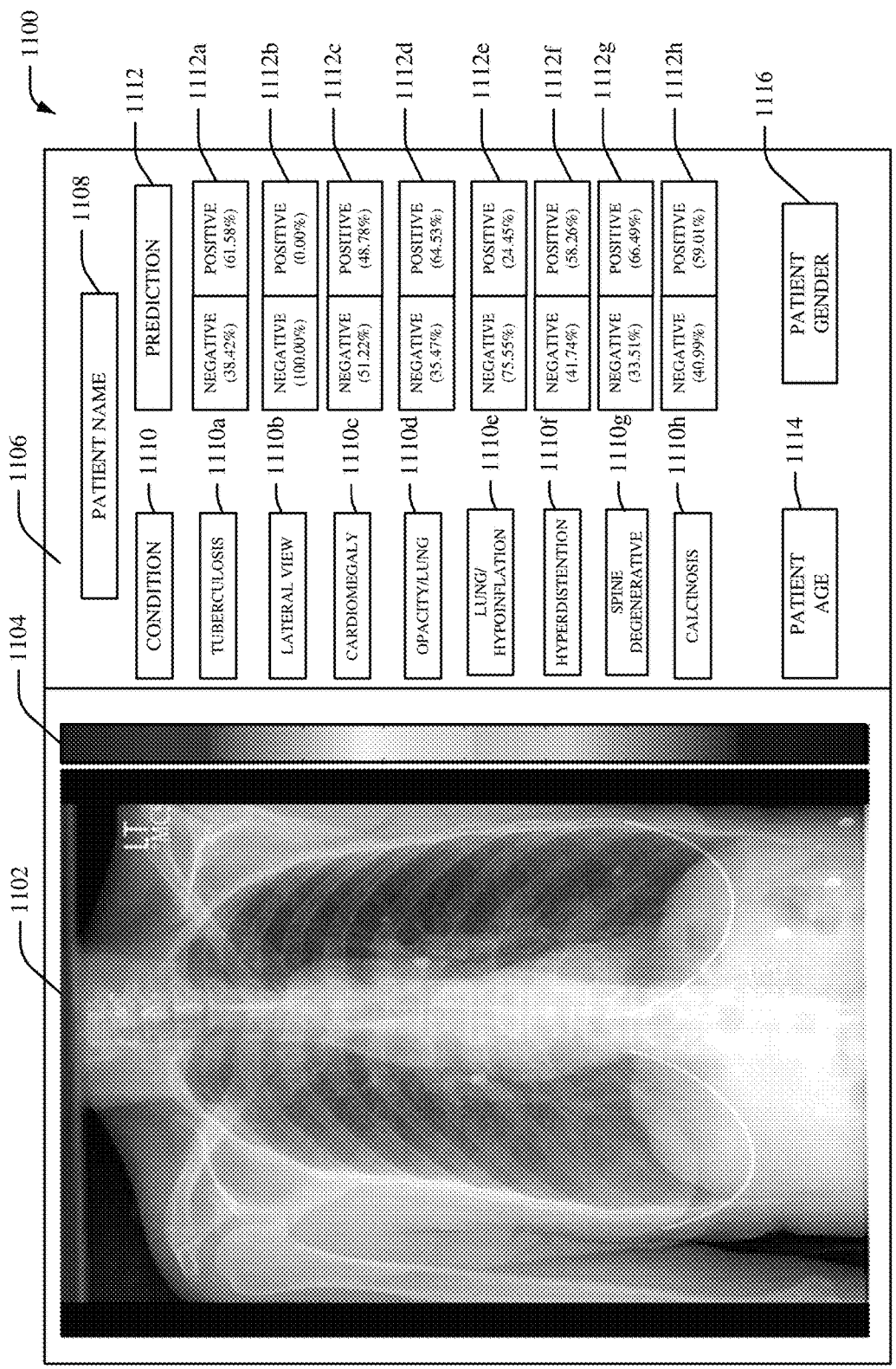
FIG. 11 illustrates an example user interface, in accordance with various aspects and implementations described herein.

FIG. 11 illustrates an example user interface 1100, in accordance with various aspects and implementations described herein. The user interface 1100 can be a display environment for medical imaging data and/or deep learning data associated with medical imaging data. The user interface 1100 can include medical imaging data 1102. In one embodiment, the medical imaging data 1102 can be displayed as a multi-dimensional visualization that presents a medical imaging diagnosis for a patient. For example, in certain embodiments, the medical imaging data 1102 can be displayed as a multi-dimensional visualization that presents one or more classifications and/or one or more localizations for one or more diseases identified in medical imaging data 1102. In certain embodiments, the medical imaging data 1102 can be displayed as a multi-dimensional visualization that presents localization data for a medical imaging diagnosis. In another embodiment, the user interface 1100 can include a heat bar 1104. The heat bar 1104 can include a set of colors that correspond to different values for the localization data. The user interface 1100 can also include a prediction section 1106 to present one or more predictions associated with the medical imaging data 1102. The prediction section 1106 can include a patient name 1108 for a patient (e.g., a patient body) associated with the medical imaging data 1102. The prediction section 1106 can also include a condition portion 1110 and a prediction portion 1112. The condition portion 1110 can include one or more conditions such as, for example, a tuberculosis condition 1110*a*, a lateral view condition 1110*b*, a cardiomegaly condition 1110*c*, an opacity/lung condition 1110*d*, a lung/hypoinflation condition 1110*e*, a hyperdistention condition 1110*f*, a spine degenerative condition 1110*g*, a calcinosis condition 1110*h* and/or another type of condition. The prediction portion 1112 can include corresponding predictions 1112*a-h* for the conditions included in the condition portion 1110. For example, the prediction 1112*a* can include a prediction for the medical imaging data 1102 being associated with tuberculosis (e.g., a 38.42% chance of a negative prognosis for tuberculosis and a 61.58% chance of a positive prognosis for tuberculosis). In another example, the prediction 1112*h* can include a prediction for the medical imaging data 1102 being associated with calcinosis (e.g., a 40.99% chance of a negative prognosis for calcinosis and a 59.01% chance of a positive prognosis for calcinosis). In certain embodiments, the prediction section 1106 can also include a patient age 1114, a patient gender 1116 and/or other information regarding a patient associated with the patient name 1108. As such, in certain embodiments, the medical imaging data 1102 can be associated with multiple diseases. Furthermore, multiple inferencing models can be employed and aggregated as deep learning data shown in the user interface 1100.

Figure 12:
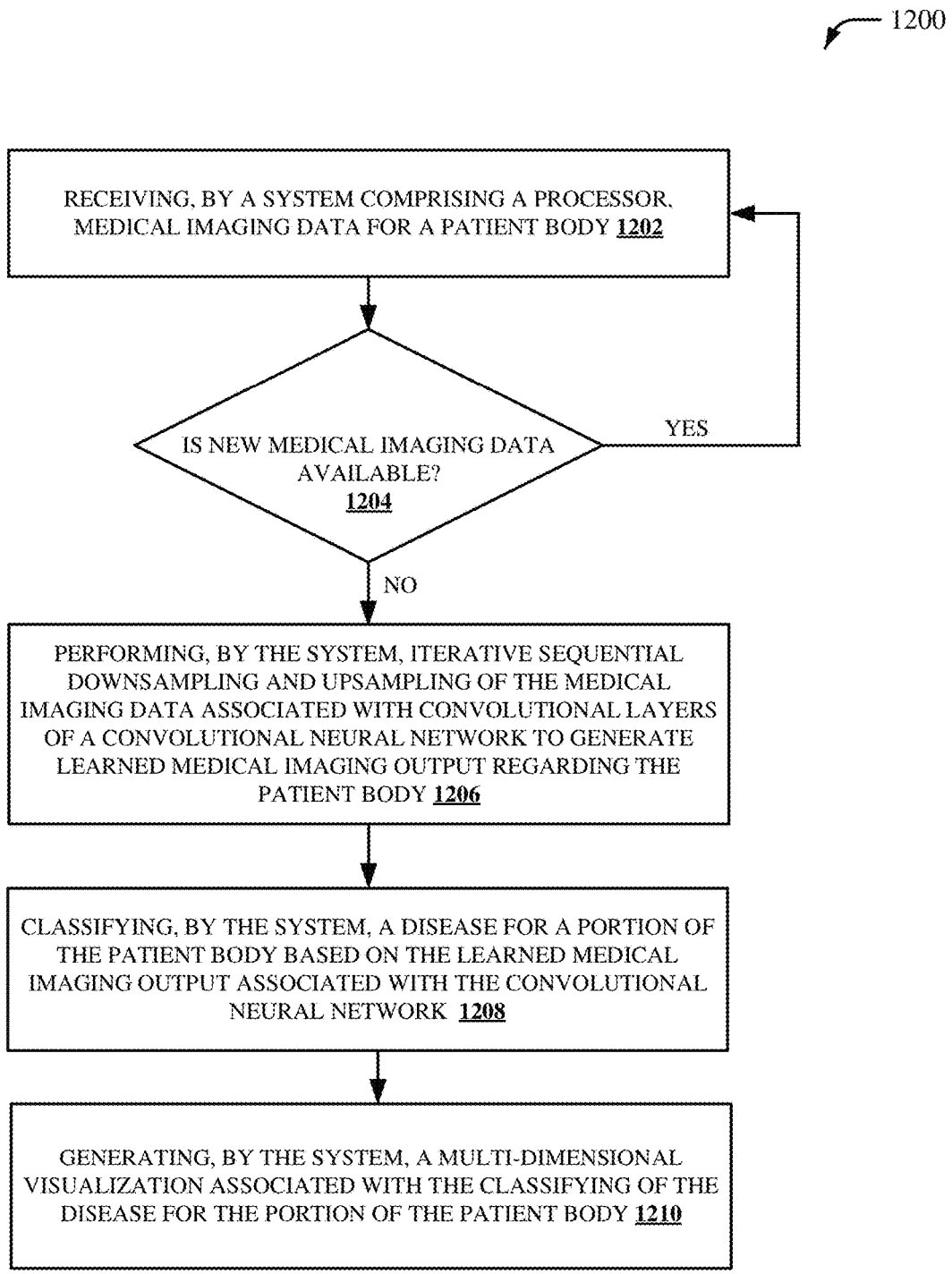
FIG. 12 depicts a flow diagram of an example method for facilitating a deep convolutional neural network with self-transfer learning, in accordance with various aspects and implementations described herein.
Figure 13:
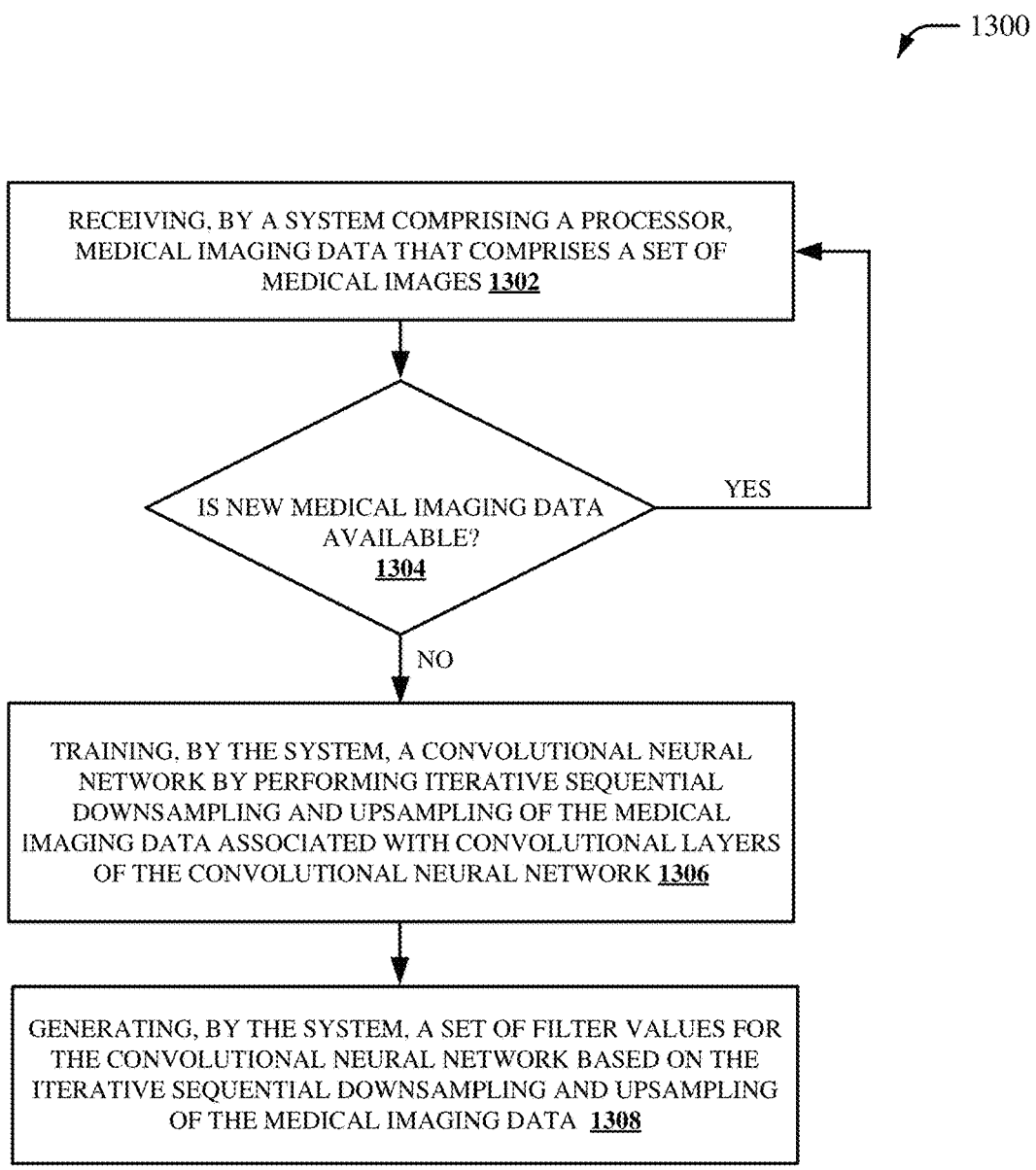
FIG. 13 depicts a flow diagram of an example method for facilitating training of a deep convolutional neural network with self-transfer learning, in accordance with various aspects and implementations described herein.

FIGS. 12-13 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 12, there is illustrated a non-limiting implementation of a methodology 1200 for facilitating a deep convolutional neural network with self-transfer learning, according to an aspect of the subject innovation. At 1202, medical imaging data for a patient body is received by a system comprising a processor (e.g., by machine learning component 104). The medical imaging data can be, for example, a medical image such as electromagnetic radiation imagery, an x-ray image, a CT scan image, another type of medical image, etc. In an embodiment, the medical imaging data can be electromagnetic radiation imagery captured via a set of sensors (e.g., a set of sensors associated with a medical imaging device).

At 1204, it is determined whether new medical imaging data is available. If yes, methodology 1200 returns to 1202. If no, methodology 1200 proceeds to 1206.

At 1206, iterative sequential downsampling and upsampling of the medical imaging data associated with convolutional layers of a convolutional neural network is performed, by the system (e.g., by machine learning component 104), to generate learned medical imaging output regarding the patient body. The iterative sequential downsampling and upsampling of the medical imaging data can behave in a spring-like manner. For example, the iterative sequential downsampling and upsampling of the medical imaging data can be associated with convolutional layer filters with various sizes. One or more convolutional layer filters can be repeated. For instance, the iterative sequential downsampling and upsampling of the medical imaging data can include a first convolutional layer filter that comprises a first size, a second convolutional layer filter that comprises a second size that is different than the first size, a third convolutional layer filter that comprises the first size associated with the first convolutional layer filter, etc. In certain embodiments, the performing the iterative sequential downsampling and upsampling of the medical imaging data can include analyzing the medical imaging data based on a first filter that comprises a first size, analyzing the medical imaging data based on a second filter that comprises a second size that is different than the first size, analyzing the medical imaging data based on a third filter that comprises the first size associated with the first filter, etc. In another embodiment, the performing the iterative sequential downsampling and upsampling of the medical imaging data can include generating the learned medical imaging output based on a first convolutional layer process associated with downsampling of the medical imaging data and a second convolutional layer process associated with upsampling of the medical imaging data. In an aspect, the performing the iterative sequential downsampling and upsampling of the medical imaging data can be associated with automated feature detection for the medical imaging data.

At 1208, a disease for a portion of the patient body classifying, by the system (e.g., by medical imaging diagnosis component 106), based on the learned medical imaging output associated with the convolutional neural network. A disease can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of disease associated with an anatomical region of a patient body. In an embodiment, a prediction for the disease can be determined. For example, a probability score for the disease can be determined (e.g., a first percentage value representing likelihood of a negative prognosis for the disease and a second value representing a likelihood of a positive prognosis for the disease can be determined).

At 1210, a multi-dimensional visualization associated with the classifying of the disease for the portion of the patient body is generated by the system (e.g., by visualization component 108. The multi-dimensional visualization can be a graphical representation of the medical imaging data that shows a classification and/or a location of one or more diseases with respect to a patient body. In an aspect, visual characteristics (e.g., color, size, hues, shading, etc.) of at least a portion of the multi-dimensional visualization can be altered based on the classification and/or a location of one or more diseases with respect to a patient body.

In certain embodiments, the methodology 1200 can additionally include performing, by the system, a local pooling process for an activation map associated with a convolutional layer of the convolutional neural network prior to performing a global pooling process associated with the convolutional neural network. In certain embodiments, the methodology 1200 can additionally or alternatively include generating, by the system, the learned medical imaging output based on a class activation mapping process that applies a set of weights to a set of heat maps associated with the medical imaging data. Furthermore, in certain embodiments, the methodology 1200 can additionally or alternatively include merging, by the system, a set of classifier layers associated with the convolutional neural network and a set of activation maps associated with the convolutional neural network to generate the learned medical imaging output.

Referring to FIG. 13, there is illustrated a non-limiting implementation of a methodology 1300 for facilitating training of a deep convolutional neural network with self-transfer learning, according to an aspect of the subject innovation. At 1302, medical imaging data that comprises a set of medical images is received by a system comprising a processor (e.g., by machine learning component 104). The medical imaging data can be, for example, a set of medical images stored in a data store. In one example, the set of medical images can be a set of x-ray images and/or a set of CT scan images.

At 1304, it is determined whether new medical imaging data is available. If yes, methodology 1300 returns to 1302. If no, methodology 1300 proceeds to 1306.

At 1306, a convolutional neural network is training, by the system (e.g., by training component 602), by performing iterative sequential downsampling and upsampling of the medical imaging data associated with convolutional layers of the convolutional neural network. The iterative sequential downsampling and upsampling of the medical imaging data can behave in a spring-like manner. For example, the iterative sequential downsampling and upsampling of the medical imaging data can be associated with convolutional layer filters with various sizes. One or more convolutional layer filters can be repeated. For instance, the iterative sequential downsampling and upsampling of the medical imaging data can include a first convolutional layer filter that comprises a first size, a second convolutional layer filter that comprises a second size that is different than the first size, a third convolutional layer filter that comprises the first size associated with the first convolutional layer filter, etc.

At 1308, a set of filter values for the convolutional neural network is generated, by the system (e.g., by training component 602), based on the iterative sequential downsampling and upsampling of the medical imaging data. For example, a set of weights for a set of filters associated with the convolutional neural network can be generated based on the iterative sequential downsampling and upsampling of the medical imaging data.

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 14:
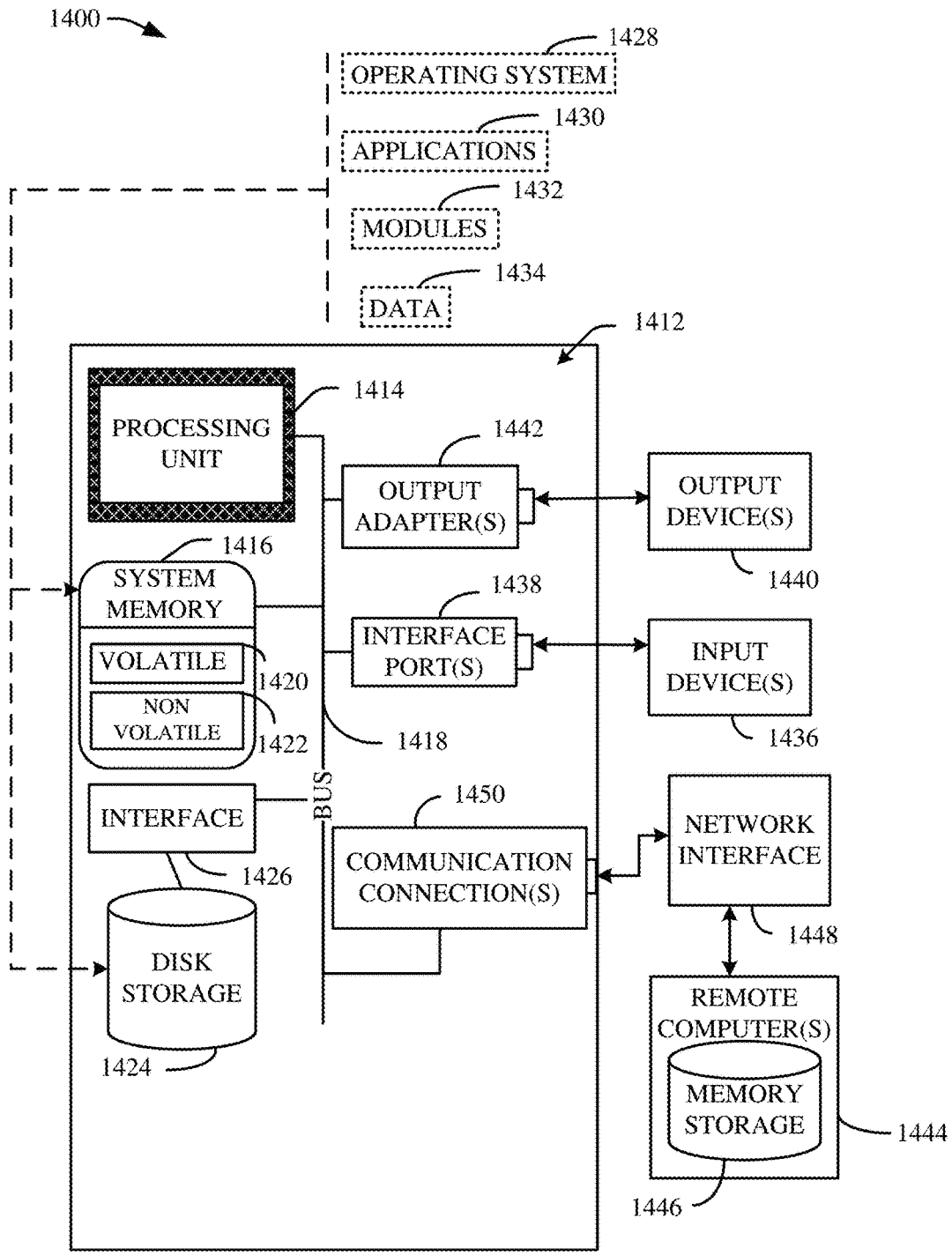
FIG. 14 is a schematic block diagram illustrating a suitable operating environment.
Figure 15:
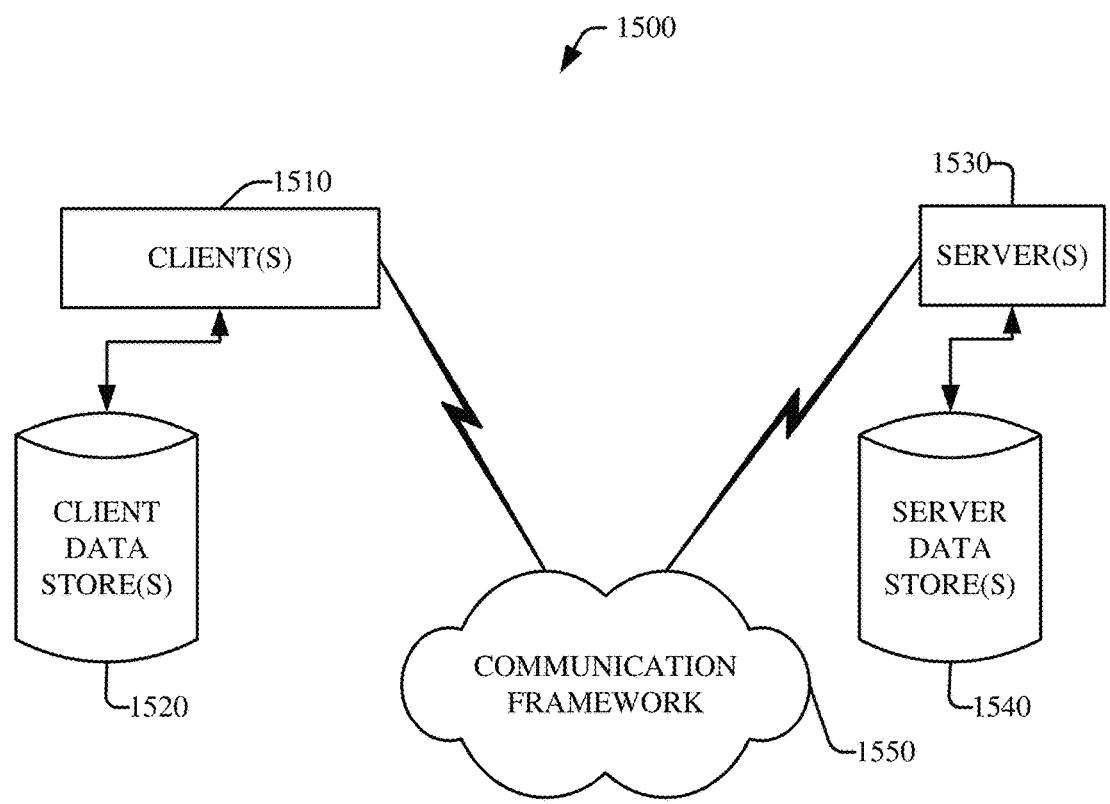
FIG. 15 is a schematic block diagram of a sample-computing environment.

In order to provide a context for the various aspects of the disclosed subject matter, FIGS. 14 and 15 as well as the following discussion are intended to provide a brief, general description of a suitable environment in which the various aspects of the disclosed subject matter may be implemented. With reference to FIG. 14, a suitable environment 1400 for implementing various aspects of this disclosure includes a computer 1412. The computer 1412 includes a processing unit 1414, a system memory 1416, and a system bus 1418. The system bus 1418 couples system components including, but not limited to, the system memory 1416 to the processing unit 1414. The processing unit 1414 can be any of various available processors. Dual microprocessors and other multiprocessor architectures also can be employed as the processing unit 1414.

The system bus 1418 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1416 includes volatile memory 1420 and nonvolatile memory 1422. The basic input/output system (BIOS), containing the basic routines to transfer information between elements within the computer 1412, such as during start-up, is stored in nonvolatile memory 1422. By way of illustration, and not limitation, nonvolatile memory 1422 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1420 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1412 also includes removable/non-removable, volatile/non-volatile computer storage media. FIG. 14 illustrates, for example, a disk storage 1424. Disk storage 1424 includes, but is not limited to, devices like a magnetic disk drive, floppy disk drive, tape drive, Jaz drive, Zip drive, LS-100 drive, flash memory card, or memory stick. The disk storage 1424 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1424 to the system bus 1418, a removable or non-removable interface is typically used, such as interface 1426.

FIG. 14 also depicts software that acts as an intermediary between users and the basic computer resources described in the suitable operating environment 1400. Such software includes, for example, an operating system 1428. Operating system 1428, which can be stored on disk storage 1424, acts to control and allocate resources of the computer system 1412. System applications 1430 take advantage of the management of resources by operating system 1428 through program modules 1432 and program data 1434, e.g., stored either in system memory 1416 or on disk storage 1424. It is to be appreciated that this disclosure can be implemented with various operating systems or combinations of operating systems.

A user enters commands or information into the computer 1412 through input device(s) 1436. Input devices 1436 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1414 through the system bus 1418 via interface port(s) 1438. Interface port(s) 1438 include, for example, a serial port, a parallel port, a game port, and a universal serial bus (USB). Output device(s) 1440 use some of the same type of ports as input device(s) 1436. Thus, for example, a USB port may be used to provide input to computer 1412, and to output information from computer 1412 to an output device 1440. Output adapter 1442 is provided to illustrate that there are some output devices 1440 like monitors, speakers, and printers, among other output devices 1440, which require special adapters. The output adapters 1442 include, by way of illustration and not limitation, video and sound cards that provide a means of connection between the output device 1440 and the system bus 1418. It should be noted that other devices and/or systems of devices provide both input and output capabilities such as remote computer(s) 1444.

Computer 1412 can operate in a networked environment using logical connections to one or more remote computers, such as remote computer(s) 1444. The remote computer(s) 1444 can be a personal computer, a server, a router, a network PC, a workstation, a microprocessor based appliance, a peer device or other common network node and the like, and typically includes many or all of the elements described relative to computer 1412. For purposes of brevity, only a memory storage device 1446 is illustrated with remote computer(s) 1444. Remote computer(s) 1444 is logically connected to computer 1412 through a network interface 1448 and then physically connected via communication connection 1450. Network interface 1448 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1450 refers to the hardware/software employed to connect the network interface 1448 to the bus 1418. While communication connection 1450 is shown for illustrative clarity inside computer 1412, it can also be external to computer 1412. The hardware/software necessary for connection to the network interface 1448 includes, for exemplary purposes only, internal and external technologies such as, modems including regular telephone grade modems, cable modems and DSL modems, ISDN adapters, and Ethernet cards.

FIG. 15 is a schematic block diagram of a sample-computing environment 1500 with which the subject matter of this disclosure can interact. The system 1500 includes one or more client(s) 1510. The client(s) 1510 can be hardware and/or software (e.g., threads, processes, computing devices). The system 1500 also includes one or more server(s) 1530. Thus, system 1500 can correspond to a two-tier client server model or a multi-tier model (e.g., client, middle tier server, data server), amongst other models. The server(s) 1530 can also be hardware and/or software (e.g., threads, processes, computing devices). The servers 1530 can house threads to perform transformations by employing this disclosure, for example. One possible communication between a client 1510 and a server 1530 may be in the form of a data packet transmitted between two or more computer processes.

The system 1500 includes a communication framework 1550 that can be employed to facilitate communications between the client(s) 1510 and the server(s) 1530. The client(s) 1510 are operatively connected to one or more client data store(s) 1520 that can be employed to store information local to the client(s) 1510. Similarly, the server(s) 1530 are operatively connected to one or more server data store(s) 1540 that can be employed to store information local to the servers 1530.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A convolutional neural network system, comprising:
a memory that stores computer executable components;
a processor that executes computer executable components stored in the memory, wherein the computer executable components comprise:
a machine learning component that generates learned medical imaging output regarding an anatomical region based on a convolutional neural network that receives medical imaging data, wherein the machine learning component performs a first convolutional layer process associated with sequential downsampling of the medical imaging data followed by a second convolutional layer process associated with sequential upsampling of the medical imaging data, and wherein a first convolutional layer of the first convolutional layer process corresponds to a last convolutional layer of the second convolutional layer process;
a medical imaging diagnosis component that determines a classification and an associated localization for a portion of the anatomical region based on the learned medical imaging output associated with the convolutional neural network; and
a visualization component that generates a multi-dimensional visualization associated with the classification and the localization for the portion of the anatomical region.

2. The convolutional neural network system of claim 1, wherein the machine learning component performs the first convolutional layer process based on a first convolutional layer filter that comprises a first size and a second convolutional layer filter that comprises a second size that is different than the first size, and wherein the machine learning process performs the second convolution layer process based on the first convolutional layer filter that comprises the first size and the second convolutional layer filter that comprises the second size.

3. The convolutional neural network system of claim 1, wherein the machine learning component performs a local pooling process for an activation map associated with a convolutional layer of the convolutional neural network prior to performing a global pooling process associated with the convolutional neural network.

4. The convolutional neural network system of claim 1, wherein the machine learning component performs the sequential upsampling of the medical imaging data in a reverse sampling sequence with respect to the sequential downsampling of the medical imaging data.

5. The convolutional neural network system of claim 1, wherein the machine learning component generates the learned medical imaging output based on a class activation mapping process that applies a set of weights to a set of heat maps associated with the medical imaging data.

6. The convolutional neural network system of claim 1, wherein the machine learning component merges a set of classifier layers associated with the convolutional neural network and a set of activation maps associated with the convolutional neural network to generate the learned medical imaging output.

7. The convolutional neural network system of claim 1, wherein the machine learning component processes the medical imaging data based on one or more regularization techniques to classify one or more portions of the medical imaging data.

8. The convolutional neural network system of claim 1, wherein the machine learning component employs a first portion of the medical imaging data for training associated with the convolutional neural network, a second portion of the medical imaging data for validation associated with the convolutional neural network, and a third portion of the medical imaging data for testing associated with the convolutional neural network.

9. The convolutional neural network system of claim 1, wherein the machine learning component randomly selects a set of medical images from a training set associated with the medical imaging data for data augmentation associated with the medical imaging data.

10. The convolutional neural network system of claim 9, wherein the machine learning component modifies an orientation of the set of medical images for the data augmentation associated with the medical imaging data.

11. The convolutional neural network system of claim 9, wherein the machine learning component modifies the set of medical images through at least one affine transformation for the data augmentation associated with the medical imaging data.

12. A method, comprising:
receiving, by a system comprising a processor, medical imaging data for a patient body;
performing, by the system, iterative sequential downsampling and upsampling of the medical imaging data associated with convolutional layers of a convolutional neural network to generate learned medical imaging output regarding the patient body, wherein a first convolutional layer for the downsampling corresponds to a last convolutional layer for the upsampling;
classifying, by the system, a disease for a portion of the patient body based on the learned medical imaging output associated with the convolutional neural network; and
generating, by the system, a multi-dimensional visualization associated with the classifying of the disease for the portion of the patient body.

13. The method of claim 12, wherein the performing the iterative sequential downsampling and upsampling of the medical imaging data comprises:
analyzing the medical imaging data based on a first filter that comprises a first size;
analyzing the medical imaging data based on a second filter that comprises a second size that is different than the first size; and
analyzing the medical imaging data based on a third filter that comprises the first size associated with the first filter.

14. The method of claim 12, further comprising:
performing, by the system, a local pooling process for an activation map associated with a convolutional layer of the convolutional neural network prior to performing a global pooling process associated with the convolutional neural network.

15. The method of claim 12, wherein the performing the iterative sequential downsampling and upsampling of the medical imaging data comprises generating the learned medical imaging output based on a first convolutional layer process associated with downsampling of the medical imaging data and a second convolutional layer process associated with upsampling of the medical imaging data.

16. The method of claim 12, further comprising:
generating, by the system, the learned medical imaging output based on a class activation mapping process that applies a set of weights to a set of heat maps associated with the medical imaging data.

17. The method of claim 12, further comprising:
merging, by the system, a set of classifier layers associated with the convolutional neural network and a set of activation maps associated with the convolutional neural network to generate the learned medical imaging output.

18. A method, comprising:
receiving, by a system comprising a processor, medical imaging data that comprises a set of medical images;
training, by the system, a convolutional neural network by performing a first convolutional layer process associated with downsampling of the medical imaging data followed by a second convolutional layer process associated with upsampling of the medical imaging data, wherein an initial convolutional layer of the first convolutional layer process corresponds to a last convolutional layer of the second convolutional layer process; and
generating, by the system, a set of filter values for the convolutional neural network based on the first convolutional layer process associated with the downsampling and the second convolutional layer process associated with the upsampling.

19. The method of claim 18, wherein the training comprises:
analyzing the medical imaging data based on a first convolutional layer filter that comprises a first size;
analyzing the medical imaging database on a second convolutional layer filter that comprises a second size that is different than the first size; and
analyzing the medical imaging database on a third convolutional layer filter that comprises the first size associated with the first convolutional layer filter.

20. The method claim 18, wherein the generating the set of filter values comprises generating a set of weights for the convolutional neural network based on the first convolutional layer process associated with the downsampling and the second convolutional layer process associated with the upsampling.

* * * * *